United States Patent [19]

Arulanandan et al.

[11] Patent Number: 4,654,598

[45] Date of Patent: Mar. 31, 1987

[54] DIELECTRIC METHODS AND APPARATUS FOR IN SITU PREDICTION OF POROSITY AND SPECIFIC SURFACE AREA (I.E., SOIL TYPE) AND FOR DETECTION OF HYDROCARBONS, HAZARDOUS WASTE MATERIALS, AND THE DEGREE OF MELTING OF ICE AND TO PREDICT IN SITU STRESS-STRAIN BEHAVIOR

[75] Inventors: Kandiah Arulanandan; Shiva Arulanandan, both of Davis, Calif.

[73] Assignee: The Regents of The University of California, Berkeley, Calif.

[21] Appl. No.: 709,592

[22] Filed: Mar. 8, 1985

[51] Int. Cl.⁴ .................. G01R 27/02; G01V 3/06; G01N 27/02

[52] U.S. Cl. .................. 324/354; 324/57 R; 324/61 P; 324/65 P; 324/347; 324/449

[58] Field of Search .................. 324/57 R, 61 R, 61 P, 324/65 R, 65 P, 149, 323–325, 332, 333, 347, 348, 354, 355, 439, 444, 446–449, 376

[56] References Cited

U.S. PATENT DOCUMENTS

| | | | |
|---|---|---|---|
| 1,910,021 | 5/1933 | Legg | 324/65 R |
| 2,390,409 | 12/1945 | Aiken | 324/355 |
| 2,745,057 | 5/1956 | Dotson | 324/376 |
| 2,802,172 | 8/1957 | Mueller et al. | 324/376 |
| 2,922,103 | 1/1960 | Smith | 324/324 |
| 3,302,102 | 1/1967 | Lace | 324/449 |
| 3,582,768 | 6/1971 | Watson | 324/449 |
| 3,657,640 | 4/1972 | Jelinek et al. | 324/65 P X |
| 3,870,951 | 3/1975 | Brown et al. | 324/61 P |
| 4,219,776 | 8/1980 | Arulanandan | 324/323 |

Primary Examiner—Gerard R. Strecker
Attorney, Agent, or Firm—Owen, Wickersham & Erickson

[57] ABSTRACT

A soil probe, comprising, in one form, a cylindrical member of insulating material having a pair of metal, electrically conductive, ring electrodes mounted a short distance above a conical portion at the lower end of the probe, these ring electrodes lie flush with the outer surface of the cylindrical member and are spaced apart from each other by the insulating material. An electrical-electronic measuring system is connected to the electrodes by conductors providing identical line impedance for each ring. The system has an initial electronic portion inside the cylindrical member and close to the electrodes and has a second portion distant from the cylindrical member. A plurality of different frequencies of radio-frequency current is applied to the electrodes, for accurate determination of capacitance at the different frequencies. Therefrom are determined the dielectric dispersion characteristics of the soil. A soil probe with three electrodes in a cylindrical tube can be used to predict the stress-strain behavior in situ and properties such as $\lambda$, $\kappa$, and $M$ from such measured properties and $(A^2/f)$, $\Delta\epsilon$, and $(e_1/e_t)$ versus $\kappa$.

20 Claims, 24 Drawing Figures

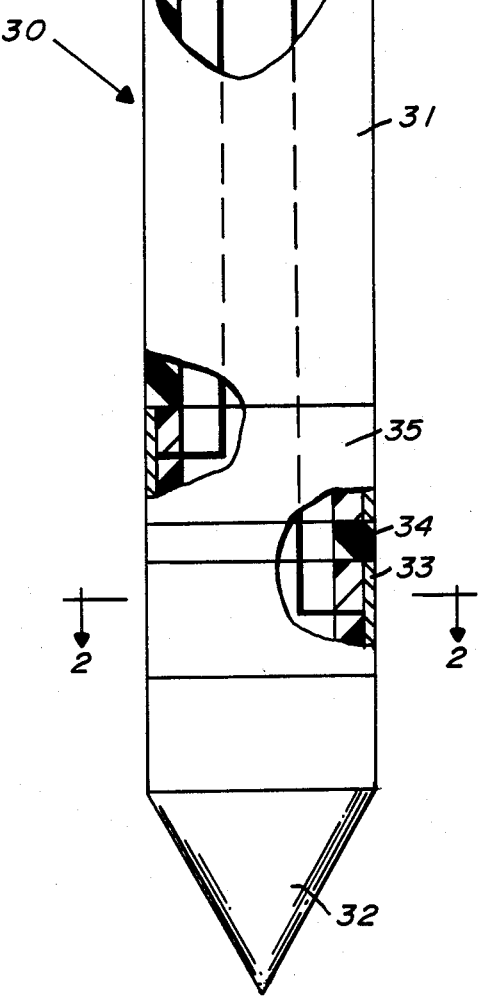
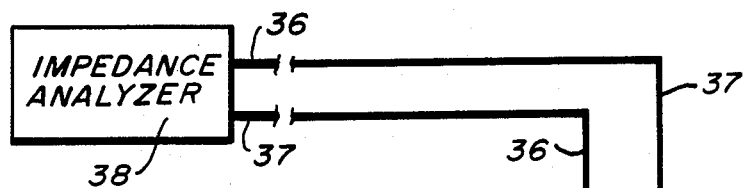
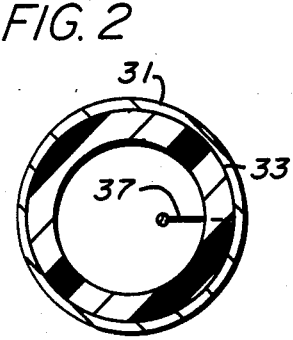
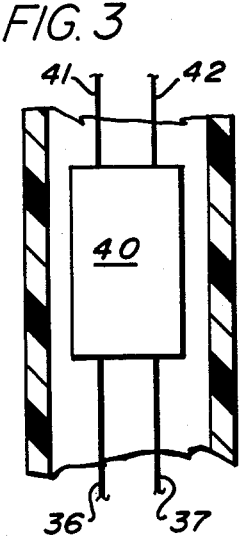

VARIATION OF DIELECTRIC CONSTANT AND CONDUCTIVITY AS A FUNCTION OF FREQUENCY FOR SANDS AND SILTS

EFFECT OF CLAY TYPE AND AMOUNT ON MAGNITUDE
OF DIELECTRIC DISPERSION

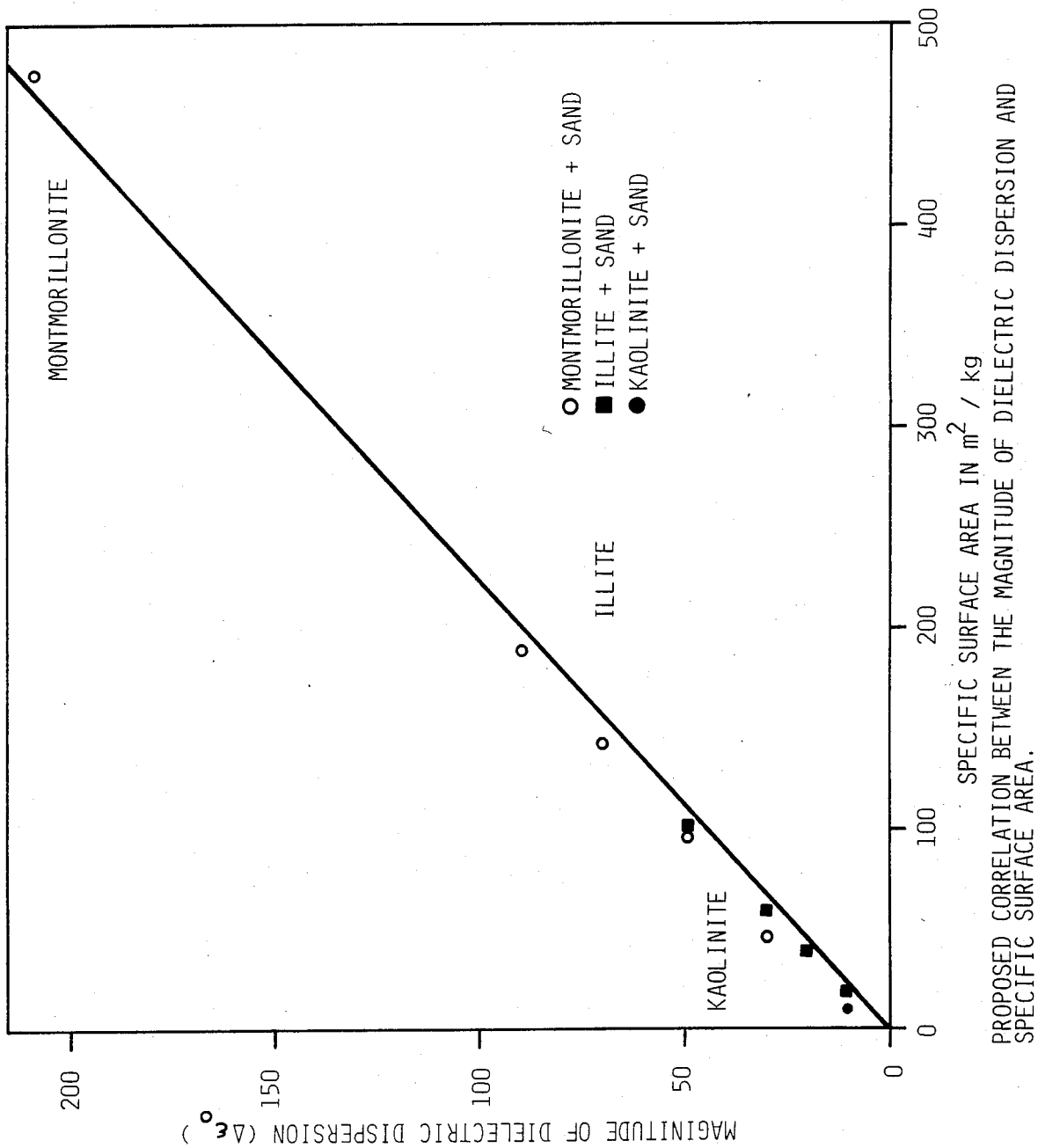

DIELECTRIC-CONDUCTIVITY DISPERSION CHARACTERISTICS OF MONTMORILLONITE PASTE AT 700% WATER CONTENT MEASURED USING THE DIELECTRIC-CONDUCTIVITY CONE PROBE

DIELECTRIC — CONDUCTIVITY DATA USING DIELECTRIC — CONDUCTIVITY CONE PROBE

ELECTRICAL DISPERSION DATA FOR 5% BENTONITE + 95% MONTEREY SAND WITH DIFFERENT PERCENTAGES OF TOLUENE – IMPEDANCE ANALYZER

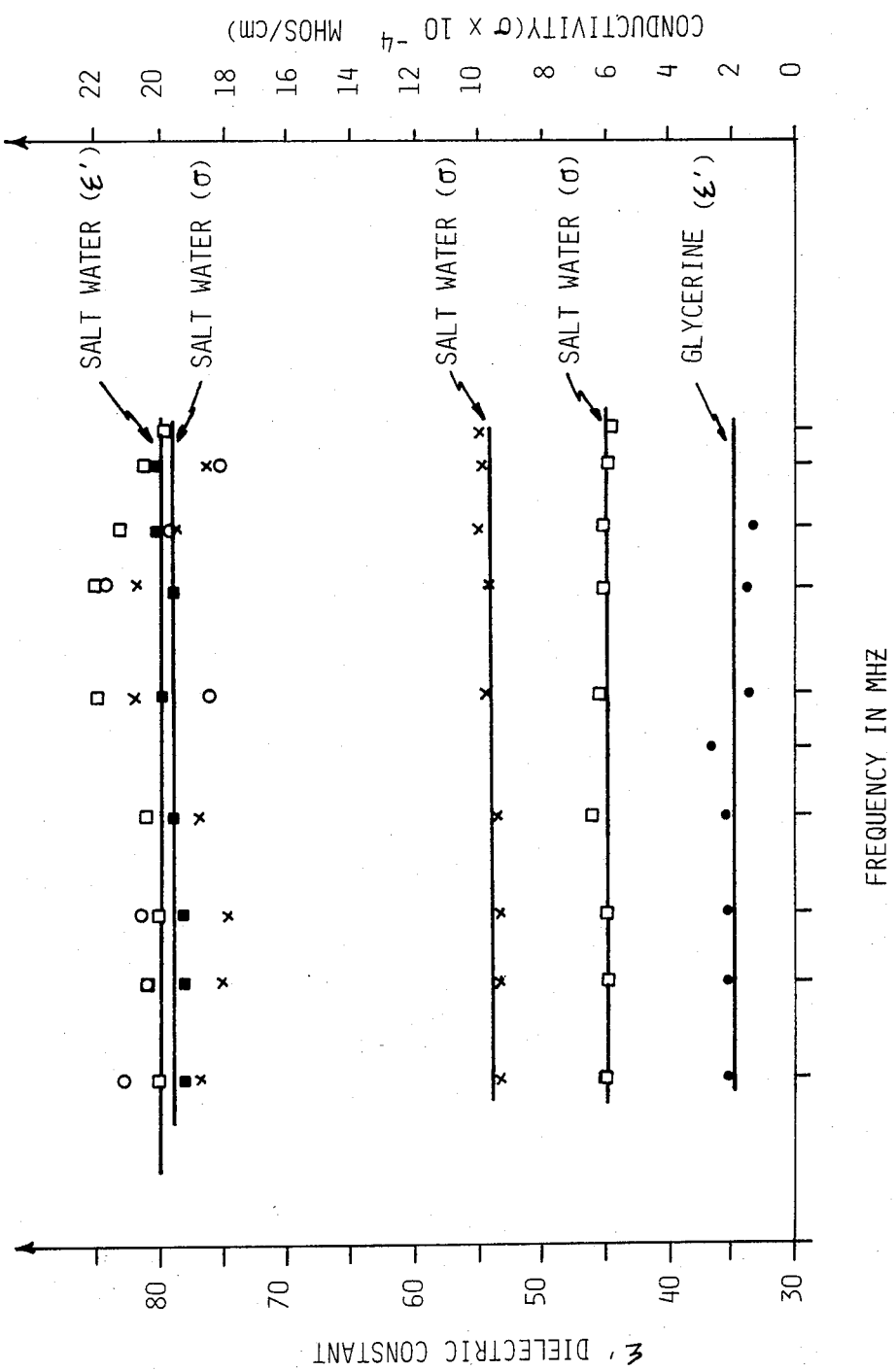

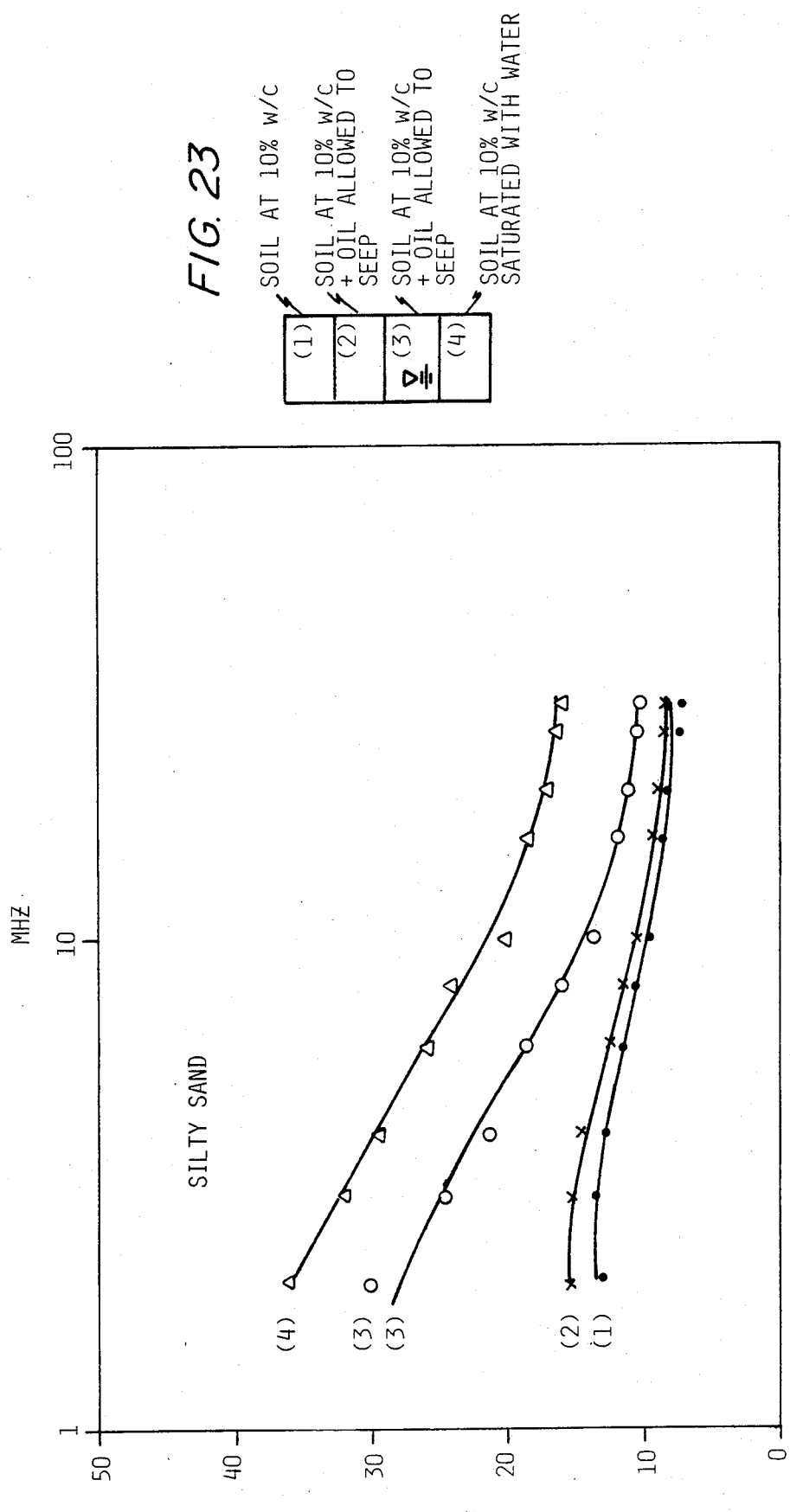

DIELECTRIC METHODS AND APPARATUS FOR IN SITU PREDICTION OF POROSITY AND SPECIFIC SURFACE AREA (I.E., SOIL TYPE) AND FOR DETECTION OF HYDROCARBONS, HAZARDOUS WASTE MATERIALS, AND THE DEGREE OF MELTING OF ICE AND TO PREDICT IN SITU STRESS-STRAIN BEHAVIOR

This invention relates to soil classification employing dielectric dispersions. It also relates to such specific applications as detecting soil strata which are contaminated by oil or which contain much water or other ingredients affecting soils; differences are thereby detected that distinguish, from each other, soils which may otherwise have the same basic structure.

BACKGROUND OF THE INVENTION

One pressing need for better soil classification techniques than have been available before, is the need to locate contaminating petroleum products, hazardous waste materials, and the like. For example, at refineries and old filling station sites, petroleum products such as crude oil and gasoline have sometimes been spilled or have leaked onto the soil and have seeped downwardly through the soil. It is of great assistance in cleaning up such contamination to know exactly where this material is principally concentrated, and the present invention makes this possible. The concentration may be anywhere from just below the ground surface down to one hundred feet or more below ground, and the present invention makes it possible to detect the location of such a concentration. The invention therefore makes it that much easier to remove the contaminated layer of soil. This will be explained further and in detail below.

This is only one example of the many instances in which it is important to know the characteristics of soil. For example, another example is the desirability of detecting below-ground (or on level ground) ice and its state of complete solidity or partial melting.

Two types of soils are recognized as basic: non-clay minerals, typified by sands, and clay minerals, typified by clays.

Present methods of classification of soil between clays and sands have been based on an arbitrary line of demarcation at a particle size of 2 microns (0.002 mm); smaller-particle soils have been treated as clay, and larger-particle soils have been treated as sand. However, this arbitrary boundary does not always correspond with the plasticity of such soil. It is possible for soils to exhibit the plasticity characteristics of clay in the presence of water, both above and below the 2 micron level of particle size, and it is also possible for soils to be properly classified as non-clay minerals above and below that level.

The present invention provides a quantitative and fundamental demarcation between clays and sands, by using the dielectric dispersion characteristics of the soils to indicate whether the soil is really a clay or a sand.

It is also important to quantify the intercluster and intracluster natures of soils and the void ratios shown by such clusters in cohesive soils or clays.

Other soil characteristics mentioned below, are also extremely desirable to determine.

One trouble with prior art methods of determinating soil characteristics was the amount of time those methods required. First, the soil layer had to be uncovered or drilled into. Then a sample was taken. Then that sample was taken away and subjected to laboratory apparatus, usually remote from the original site. In situ equipment was sometimes used, but with varying degrees of success; indeed, in situ methods were limited largely to determining only a few of the characteristics needed.

Several different in situ testing techniques are in current use for evaluation of the soil properties that establish one or more empirical criteria for the prediction of the potential behavior of soils. The standard penetration test and the cone penetration test are widely used and are very useful; others include pressure meter tests and bore hole shear tests; also, dilatometers are being used on a moderate scale. However, the reliability and usefulness of the test results obtained from these various techniques are limited because of several reasons. The drainage conditions in the soils during the in situ testing may be unknown. The failure modes may not simulate those anticipated for the actual product, and in some cases the exact failure mode is unknown. Due to the unknown drainage and failure conditions and the specific nature of the testing procedures and the failure mode simulated in different techniques, the interpretation of the test results has been highly empirical. For the same reason generalization of the test results has been very difficult.

The present invention makes it possible to investigate soils in situ and to do so very quickly. For instance, some determinations that formerly took a day to determine once the soil was reached, can now be done in less than five minutes by employing the present invention.

The present invention has both method and apparatus aspects. Its apparatus aspects provide a system by which the needed measurements can be taken, and the method includes not only the method of taking these measurements, but also methods of using them to determine the characteristics of the soil.

SUMMARY OF THE INVENTION

In its apparatus aspects the invention comprises a novel soil probe and a probe apparatus incorporating electrical circuitry. One preferred form of the probe of this invention is a cylindrical member terminating in a conical portion at its lower end; the conical lower end may be a 60° steel cone tip, while the cylindrical portion comprises a cylinder of electrical-insulating material provided with a pair of spaced-apart conductive rings located a short distance above the conical lower end and flush with the surface of the cylindrical portion. These rings may be brass or copper and are spaced apart from each other by electrical insulating portions of the cylinder, which is made from ceramic or insulating plastic of a suitable nature, such as polytetrafluoroethylene or poly(amide-imide). The two brass rings are used as electrodes spaced vertically from each other.

The rings are connected to a suitable electrical-electronic measuring system. This system basically includes means for providing identical line impedance for each ring, as by providing an identical length of conductor between the probe and its initial electronic system, and between that initial electronic system and a later electronic system. Thus, the two probe rings may be and preferably are connected by two separate lines, one from each electrode-ring, to the initial electronic system, which is located only a short distance away from the probe, for as line impedances become high, due to length of the wires, accuracy of measurement decreases. This initial electronic system is then connected by a pair of identical lines (or lines having identical line impedance) to a second circuit above ground that can be directly controlled by an operator. (Alternatively, for laboratory or research work, the probe rings may be connected directly to an impedance analyzer located above ground.)

This second or above-ground electronic system of the preferred form includes a radio-frquency oscillator that can produce a plurality or series of signals at different frequencies. It also includes means for varying the magnitudes of resistance and capacitance in an R-C circuit which comprises a major portion of the initial circuit. Thus, the initial circuit generates a signal, and this is received by the second circuit and subjected there to additional electronic manipulation. The second circuit includes a phase amplitude detector connected to the initial electronic system by a high-pass filter. The detector's output is connected via an analog-to-digital converter to a computer. The data thereby obtained can then be plotted or otherwise analyzed to determine the soil characteristics according to what is desired. The computer, via a digital-to-analog converter adjusts two D-C bias power supplies that are connected to the intial circuit—one for the variable resistance and one for the variable capacitance.

By this probe and its related circuits, one can instantly tell whether a particular soil is granular or cohesive, what its water content is, and whether there is a concentration of petroleum product or of ice in the soil, for example. All this has been very difficult to do heretofore.

A second form of probe according to the present invention has three electrodes—two on the same horizontal level and one on a different level. All three are mounted on a cylindrical insulating shell, near its lower end, and all three are connected to an initial circuit above them in the probe. Again, identical line impedances must be provided, and this may be augmented in the probe by a mirror-image system of electrodes connected to the initial circuit and balanced, with respect to the detecting electrodes, before use. Then, again, the initial circuit is connected to an above-ground circuit like that already discussed, using identical lengths of lines to eliminate the line-impedance problem there.

The key to the determination of soil characteristics is the use of dielectric dispersions according to different electromagnetic frequencies at which measurements are taken across the ring electrodes. These are taken by radio-frequency alternating current, and the frequencies may vary, for example, from 1 or 2 MHz to 50 or 100 or more MHz. By standardizing the frequencies for any particular series, and by taking three or (preferably) more measurements, it is possible to determine almost immediately whether the soil is granular or cohesive, and (possibly employing a few additional points) to determine the water content. Similarly, the oil content of cohesive soils can be determined as well as that of granular soils. dr

BRIEF DESCRIPTION OF THE DRAWINGS

In the drawings:

FIG. 1 is a view in elevation of a probe embodying the principles of the invention and connected to an above-ground impedance analyzer, for laboratory type use and study. Some portions of the probe are broken away and shown in section.

FIG. 2 is a view in section of the probe of FIG. 1 taken along the line 2—2 in FIG. 1.

FIG. 3 is a fragmentary view in elevation and in section of a portion of a modified form of probe generally like that of FIG. 1.

FIG. 10 is a graph plotting the magnitude of dielectric dispersion against specific surface area for several clays.

FIG. 19 is a graph of results obtained from the probe of FIG. 1 for various concentrations of salt water and for glycerine, plotting both dielectric constants $\epsilon$ and conductivities $\sigma$ against frequency.

FIGS. 22 and 23 are another graph and another diagram of further measurements at another situation and show the variations in dielectric dispersion in an unsaturated layer, where the water table is at a particular depth, when oil is allowed to seep.

THEORY

The dielectric constant is usually expressed as the ratio of capacities with and without the presence of the dielectric. A decisive role on the value of the dielectric constant in soils is played by its moisture content, since the dielectric constant of most minerals comprising the soil skeleton is in the order of 4–6, whereas the dielectric constant of water is of the order of magnitude of 80. Therefore, any change in the amount of water in a soil has a very marked effect on its overall dielectric constant.

Figure 7:
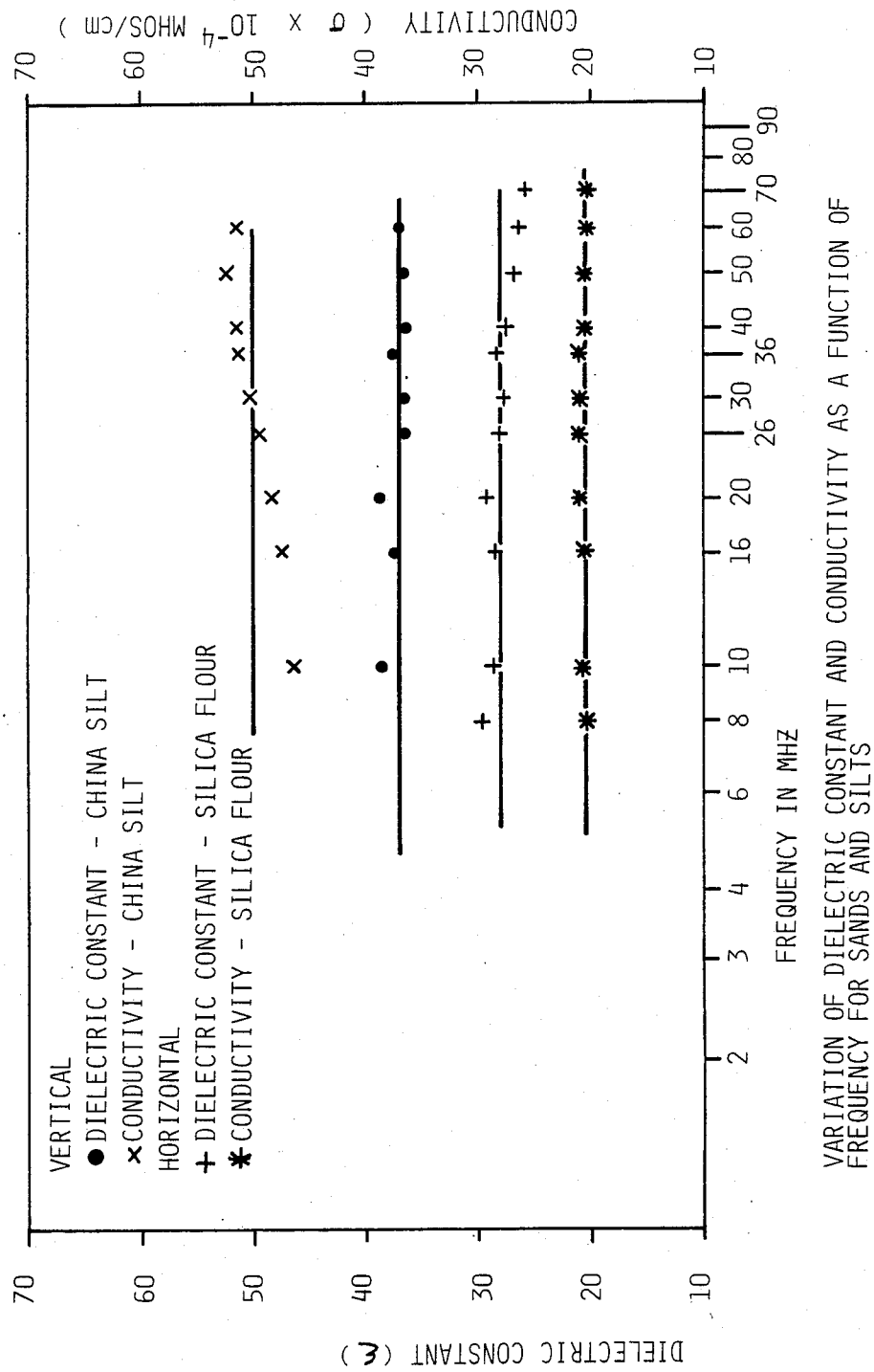
FIG. 7 is a graph of some tests on a selection of granular soils, plotting the dielectric constant $\epsilon$ and conductivity $\sigma$ against frequency. In these granular soils, these both remain substantially constant.
Figure 8:
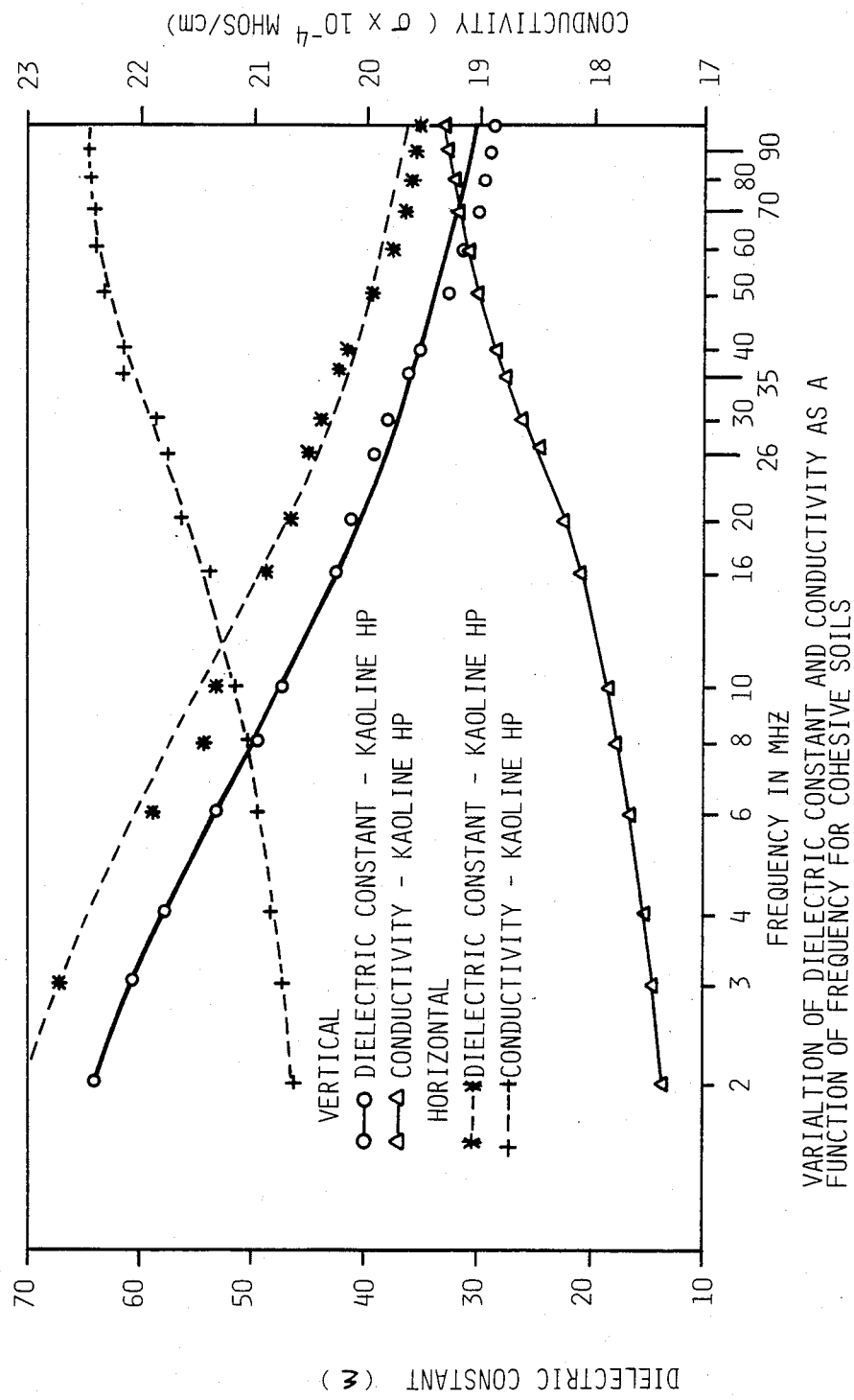
FIG. 8 is a similar graph made for some cohesive soils, where both dielectric constant $\epsilon$ and conductivity $\sigma$ vary with frequency.

When the conductivity, $\sigma$, and dielectric constant, $\epsilon$, of a cohesive system are measured as a function of frequency, in the radio frequency range, it is found that $\epsilon'$ and $\sigma$ vary as shown in FIG. 8. However, for a granular system, it is observed that $\sigma$ and $\epsilon$ are independent of frequency of frequency as shown in FIG. 7. The question arises as to the cause of the variation of $\epsilon$ as a function of frequency (dielectric dispersion) in different soil types. The understanding of the phenomenon of dielectric dispersion is necessary for the quantification of porosity and soil type.

James Clerk Maxwell showed (See *A Treatise on Electricity and Magnetism*, 3rd Edition, 1892, Articles 310–314) that the resultant conductivity $\sigma$, the conductivity of suspending medium $\sigma_s$, the conductivity of the particles $\sigma_r$, and the particle concentration, $\rho$ are related by the expression $$\sigma/\sigma_s = \frac{2 + \sigma_r/\sigma_s - 2\rho(1 - \sigma_r/\sigma_s)}{2 + \sigma_r/\sigma_s + \rho(1 - \sigma_r/\sigma_s)} \quad (1)$$

When the applied electric field is of alternating nature, one could replace the conductivity by a complex conductivity as $$\sigma_{complex} = (\sigma)_{real\,part} + jw\epsilon\epsilon_a \quad (2)$$

where
$\epsilon_a$ is the dielectric constant of air $= 8.85 \times 10^{-14}$ farad/m,
j is $-1$,
$w = 2\pi f$,
f is the frequency of the applied field,
$(\sigma)_{real}$ is the real part of complex conductivity $\sigma$, and
$\epsilon$ is the dielectric constant of the suspension.
The corresponding dielectric constant of the particle is $\epsilon_r$.

H. P. Schwan and H. Pauley in 1962, (see "Uber die Impedanzeiner Suspension Von Kugelformiten Teilchen unit einer Schale", *Z. Natuforsch* Vol. 146, pp. 125–131) assuming that an absorbed layer of thickness d' is attached to the particle, replaced $\sigma_r$ and $\epsilon_r$ by $$\sigma_r + \frac{2d'}{R}\sigma_{ad} \text{ and } \epsilon_r + \frac{2d'}{R}\epsilon_{ad},$$

ps respectively where R is the radius of equivalent sphere, and $\sigma_{ad}$ and $\epsilon_{ad}$ are the conductivity and dielectric constants of the adsorbed layer.

Using equations (1) and (2) and the assumption for $\sigma_r$ and $\epsilon_r$ as above, it is possible to obtain expressions for resultant conductivities and dielectric constants of a heterogeneous media as a function of frequency. At low frequencies, such as 2 MHz the influence of the adsorbed layer is significant due to the polarization (displacement of charges) and thus is a function of mainly soil type. At very high frequencies, of the order of 30 to 100 MHz, the polarization is nonexistent, and the dielectric constant measured is a function of particle shape, porosity and geometrical arrangement of particles and independent of mineralogy.

Thus it is possible to quantify the porosity by measuring the dielectric constant at high frequencies above 30 MHz and the soil type by observing the difference in dielectric constant obtained say at 2 MHz and 30 MHz. The validity of the hypothesis that the soil type and amount is characterized by the magnitude of dielectric dispersion $\Delta\epsilon_0$ ($\Delta\epsilon_0$=Dielectric constant at 2 MHz minus the dielectric constant at, say, 30 MHz) is shown by the results in FIG. 9.

In cohesive soils where the ratio of the surface area of an individual particle to its volume or weight (i.e., its specific surface) is large water plays an important part through its intimate relationship to the surface of the soil by surface force interaction. The effect of the presence of water and electrolyte varies with the minerals of which the soil grain is composed. The magnitude of dielectric dispersion is also a reflection of the soil type of or the mineral composition and particle shape and the amount and type of pore fluid and hence must be uniquely related to specific surface area. This hypothesis is confirmed by the results shown in FIG. 10.

It is still to be shown that the quantification of porosity is possible by measuring the dielectric constant at higher frequencies such as at 30 MHz or higher.

A more general treatment of suspensions which takes into account both the effect of particle shape and higher volume concentrations as well as the geometrical arrangement of particles in a particular direction has been presented by H. Ficke in 1953. See "The Maxwell-Wagner Dispersion in a Suspension of Ellipsoid", *Journal of Physical Chemistry*, Vol. 57, pp. 934–937. It is seen that Ficke's formulation best simulates the physical conditions found in consolidated geological materials. But the influence of particle orientation in different directions needs to be incorporated. This has been achieved by the present inventor by considering transversely isotropic media and the dielectric constants of the media measured in the vertical and horizontal directions.

The expression relating the dielectric constant of the silicate mineral $\epsilon_2$, the dielectric constant of the solution $\epsilon_1$, the horizontal dielectric constant $\epsilon_h$, the vertical dielectric constant $\epsilon_v$, the porosity n, and a parameter A defining the axial ratio for prolate spheroids a>b, b=c, so that $A_a$ is $$\frac{abc}{2} \int_0^\infty \frac{ds}{(s + a^2)\sqrt{(s + a^2)(s + b^2)(s + c^2)}}$$

and $A_b$ is $$\frac{abc}{2} \int_0^\infty \frac{ds}{(s + b^2)\sqrt{(s + a^2)(s + b^2)(s + c^2)}}, \text{ is shown as}$$

$$1/3\left[\left(\frac{\epsilon_1 - \epsilon_2}{\epsilon_v - \epsilon_2}\right) + 2\left(\frac{\epsilon_1 - \epsilon_2}{\epsilon_h - \epsilon_2}\right)\right] =$$

$$1 + \frac{1-n}{n} 1/3 \left[\frac{1}{1 + \frac{\epsilon_2 - \epsilon_1}{\epsilon_1}A_a} + \frac{2}{1 + \frac{\epsilon_2 - \epsilon_1}{\epsilon_1}A_b}\right]$$

Figure 11:
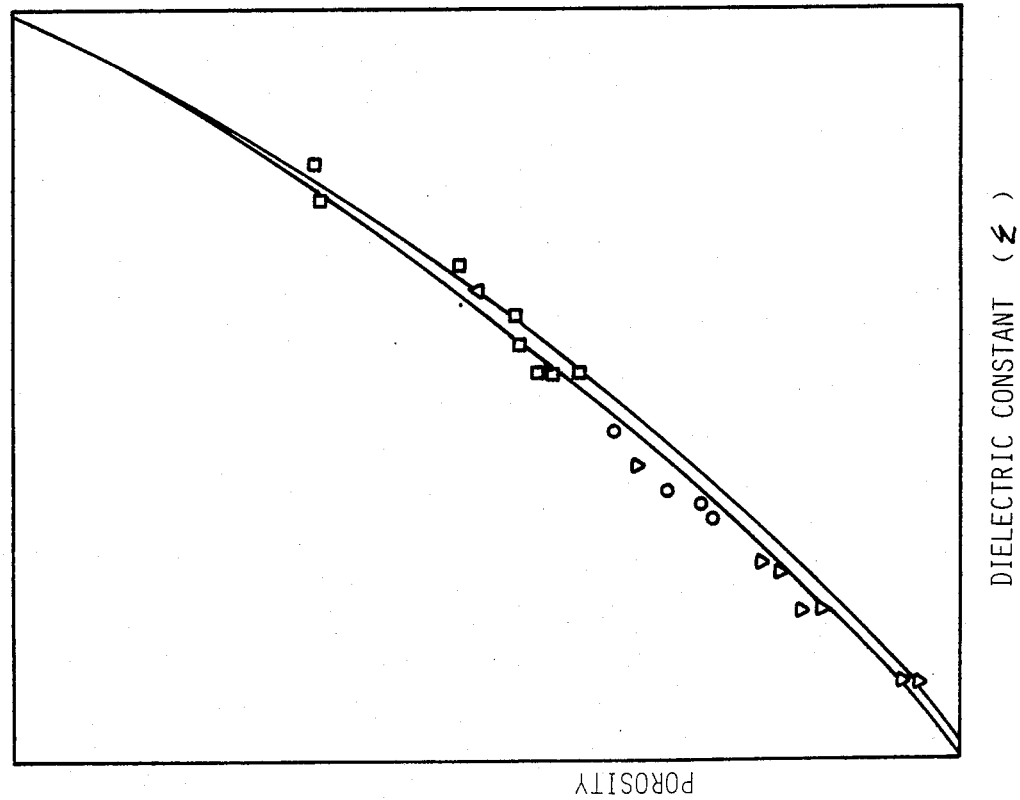
FIG. 11 is a graph of porosity versus dielectric constant, showing both a theoretical and an experimental comparison.

-continued i.e. $\dfrac{\epsilon_1 - \epsilon_2}{3}\left(\dfrac{1}{\epsilon_v - \epsilon_2} + \dfrac{2}{\epsilon_h - \epsilon_2}\right) =$ $1 + \dfrac{1-n}{n} \cdot \dfrac{1}{3}\left[\dfrac{1}{1 + \dfrac{\epsilon_2 - \epsilon_1}{\epsilon_1}A_a} + \dfrac{2}{1 + \dfrac{\epsilon_2 - \epsilon_1}{\epsilon_1}A_b}\right]$ Let $\dfrac{1}{\epsilon_v - \epsilon_2} + \dfrac{2}{\epsilon_h - \epsilon_2} =$ $1/Y$ and $\left[\dfrac{1}{1 + \dfrac{\epsilon_2 - \epsilon_1}{\epsilon_1}A_a} + \dfrac{2}{1 + \dfrac{\epsilon_2 - \epsilon_1}{\epsilon_1}A_b}\right] = f_{d\alpha}$ $\left(\dfrac{\epsilon_1 - \epsilon_2}{3}\right) 1/Y = 1 + \dfrac{1-n}{n} \cdot \dfrac{1}{3}[f_{d\alpha}]$ Thus the theoretical relationship between Y and n can be developed for $a/b = 100$ and $(a/b) = 1$, where a/b is the axial ratio assuming $\epsilon_{solution} = 79 = \epsilon_1$ and $\epsilon_{particle} = 4.5 = \epsilon_2$ as shown in FIG. 11. Plotted on this FIG. 11 are measured values for sands and clays showing the validity of using the dielectric method for the prediction of porosity. The results used to obtain the relationship shown in FIG. 11 are tabulated in Tables I to IV, as follows:

TABLE II-continued

EXPERIMENTAL RESULTS FOR Y
(A) SAND (SATURATED)

| Type of Sand | Porosity (n) | Measured $\epsilon_r$ | Measured $\epsilon_n$ | Y |
|---|---|---|---|---|
| | 0.4 | 28.0 | 30.0 | 8.26 |
| | 0.44 | 30.5 | 32.3 | 9.06 |

TABLE III

EXPERIMENTAL RESULTS FOR Y
(b) Saturated Clay

| Type of Soil | Porosity (n) | Measured $\epsilon_v$ | Measured $\epsilon_n$ | Y |
|---|---|---|---|---|
| DIFFERENT CLAYS | 0.514 | 30.4 | 37.1 | 10.0 |
| | 0.515 | 34.0 | 38.0 | 10.7 |
| | 0.521 | 34.0 | 39.7 | 11.02 |
| | 0.556 | 33.4 | 42.7 | 11.50 |
| | 0.593 | 38.0 | 41.0 | 11.81 |
| | 0.662 | 40.0 | 46.0 | 13.09 |
| | 0.756 | 50.1 | 57.5 | 16.76 |
| | 0.794 | 50.0 | 58.0 | 16.85 |

TABLE IV

EXPERIMENTAL RESULTS FOR Y
(c) Unsaturated Silty Sand

| Type of Soil | Water Content % | Voids Ratio S | Voids Ratio 1 | sn | Measured $\epsilon_v$ | Assumed Measured $\epsilon_n$ | Y |
|---|---|---|---|---|---|---|---|
| Silty Sand | 6 | — | — | 0.101 | 8.7 | 8.7 | 1.4 |
| from | 6 | — | — | 0.103 | 8.0 | 8.0 | 1.11 |
| El Segundo | 12 | — | — | 0.198 | 17.0 | 17.0 | 4.16 |
| | 12 | 53.25 | 0.603 | 0.20 | 15.3 | 15.3 | 3.6 |
| | 15 | 72.3 | 0.527 | 0.25 | 18.5 | 18.5 | 4.67 |
| | 15 | — | — | 0.266 | 20.0 | 20.0 | 5.16 |
| | — | — | — | 0.392 | 30.0 | 30.0 | 8.5 |

It is observed from the above that the experimental results are in close agreement to the theoretical values for any range of porosity and a unique relationship is obtained between Y (a function of dielectric constant) and a porosity n for any kind of soil. The theoretical values of Y are calculated for only prolate spheroids with $a > b = c$, and it is found that for any value of

TABLE I

| | | | THEORETICAL CALCULATION OF Y | | | | | | | | |
|---|---|---|---|---|---|---|---|---|---|---|---|
| b/a | $a_a$ | $a_b$ | Y AT n = 0.1 | Y AT n = 0.2 | Y AT n = 0.3 | Y AT n = 0.4 | Y AT n = 0.5 | Y AT n = 0.6 | Y AT n = 0.7 | Y AT n = 0.8 | Y AT n = 0.9 | Y AT n = 0.0 |
| 1.0 | 0.333 | 0.333 | 1.75 | 3.63 | 5.62 | 7.78 | 10.09 | 12.56 | 15.26 | 18.30 | 21.34 | 26.83 |
| 0.67 | 0.233 | 0.383 | 1.74 | 3.60 | 5.58 | 7.75 | 10.05 | 12.56 | 15.23 | 08.16 | 21.34 | 24.83 |
| 0.50 | 0.173 | 0.413 | 1.72 | 3.56 | 5.52 | 7.67 | 9.97 | 12.45 | 15.15 | 18.09 | 21.32 | 24.83 |
| 0.33 | 0.109 | 0.446 | 1.69 | 3.49 | 5.43 | 7.56 | 9.84 | 12.32 | 15.02 | 17.99 | 21.20 | 24.83 |
| 0.25 | 0.076 | 0.463 | 1.67 | 3.46 | 5.38 | 7.49 | 9.77 | 12.24 | 19.95 | 17.92 | 21.16 | 24.83 |
| 0.17 | 0.044 | 0.478 | 1.65 | 3.42 | 5.346 | 7.43 | 9.69 | 12.17 | 14.87 | 17.86 | 21.09 | 24.83 |
| 0.1 | 0.003 | 0.498 | 1.62 | 3.38 | 5.27 | 7.33 | 9.58 | 12.04 | 14.76 | 17.77 | 21.09 | 24.83 |
| 0.01 | 0.0 | 0.500 | 1.61 | 3.36 | 5.25 | 7.31 | 9.56 | 12.02 | 14.73 | 17.75 | 21.06 | 24.83 |
| 0 | 0 | 0.500 | 1.61 | 3.36 | 5.25 | 7.31 | 9.56 | 12.02 | 14.75 | 17.75 | 21.06 | 24.83 |

TABLE II

EXPERIMENTAL RESULTS FOR Y
(A) SAND (SATURATED)

| Type of Sand | Porosity (n) | Measured $\epsilon_r$ | Measured $\epsilon_n$ | Y |
|---|---|---|---|---|
| DIFFERENT SANDS | 0.32 | 23.2 | 24.5 | 6.5 |
| | 0.32 | 23.2 | 25.5 | 6.7 |
| | 0.34 | 24.0 | 25.5 | 6.82 |
| | 0.36 | 25.0 | 29.0 | 7.67 |
| | 0.4 | 28.0 | 30.0 | 8.26 |
| | 0.4 | 28.0 | 31.7 | 8.62 |
| | 0.4 | 27.0 | 29.0 | 7.93 |
| | 0.4 | 27.5 | 29.6 | 8.10 |

$R = a/b$ the variations Y with porosity (n) holds. It can therefore be concluded that Y is not only independent of orientation, but also of shape, for practical purposes. Thus, it can be concluded that the measurement of dielectric constant in different directions (horizontal and vertical) at frequencies higher than 30 MHz enables one to predict the porosity of any material.

The above analysis shows that the measurement of dielectric constant as a function of frequency in the radio frequency range (2 MHz–30 MHz) in situ provides a new approach to the quantification of porosity and specific surface

PREFERRED EMBODIMENT OF THE INVENTION

A preferred probe (FIGS. 1 to 3)

A probe 30 embodying the principles of the invention may comprise a cylindrical shank 31 having a cone 32 at its lower end. The cone 32 may be a 60° steel cone tip, and the cylindrical shank 31 may principally comprise a tubular rod of insulating material such as polytetrafluoroethylene or a poly(amide-imide). This tubular rod may be about one inch in inner diameter and about 1.7" in outer diameter. About ¾" above the upper end of the cone 32 is a first ring electrode 33, which may be of copper or brass. This ring electrode 33 may be about ⅛" wide and about ⅛" thick and is embedded in the rod 31 so that the outer periphery of the cylinder 31 is smooth. About 1" above the first electrode 33 and spaced from it by a ring portion 34 of the insulating plastic or ceramic shank 31, is a second copper or brass electrode 35 of the same dimensions as the electrode 33.

For laboratory use, each of these electrodes 33 and 35 is connected by respective copper wire 36 and 37, such as 1/16" diameter wire to an impedance analyzer 38. The wires 36 and 37 are identical in length and in line impedance, —a very important feature.

Figure 4:
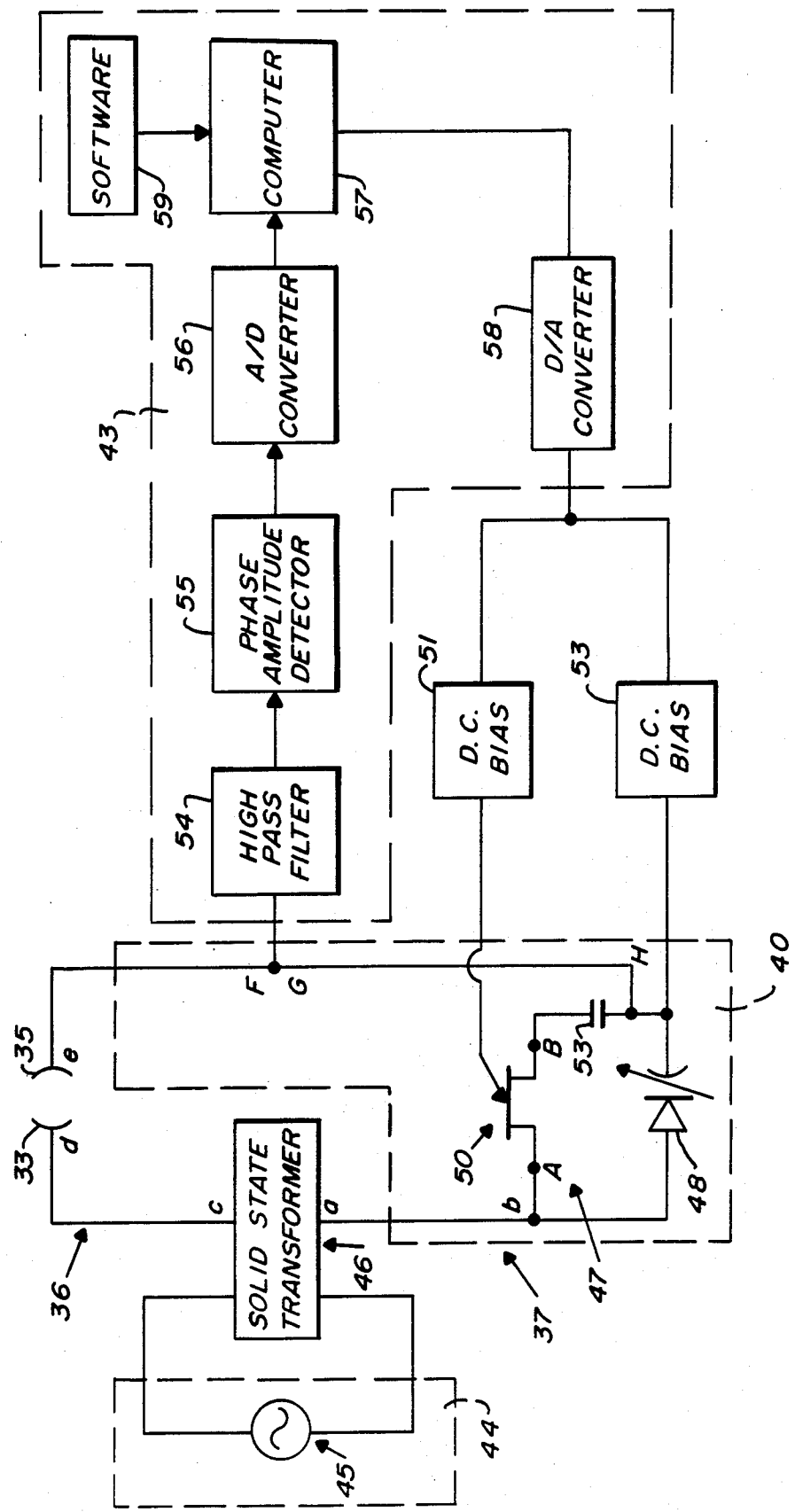
FIG. 4 is a circuit diagram, largely a block diagram, of a circuit for field use embodying the principles of the invention and using the probe of FIG. 1 with an included circuit board connected to a field-type above-ground circuit.

While the circuitry of FIG. 1 is useful for laboratory use, the circuitry of FIGS. 3 and 4 is better for field use. Here, the wires 36 and 37 are connected to a circuit board 40 located inside the tube 31 above the electrodes 33 and 35. Preferably, the circuit board 40 should be no more than 3" to 4" away from the electrodes 33 and 35 in order to minimize line inpedance and may be closer than that.

From the circuit board 40 two leads 41 and 42 go to the ground level and are connected there to the detection and control circuitry 43. The lengths of the copper conductors 41 and 42 are identical, so that their line impedances are identical. The line impedances are, of course, tested and determined to be identical.

A basic circuit (FIG. 4)

As shown in FIG. 4, the above-ground circuit 43 includes a portion 44 that, in FIG. 4 is shown separated from most of the circuit 43 although actually it may be on the same chassis. This circuit portion 44 includes a radio-frequency variable oscillator 45 is provided to generate a sinusoidal signal at a suitable amplitude, for example, one or two volts and at radio frequencies, which may be varied, for example, from about 1 MHz to about 200 MHz. An accurate indication of the exact frequency is provided and is read at each point of the test.

The signal from the oscillator 45 is divided into two sinusoidal signals as it passes through a solid state center-grounded transformer 46. The signals generated by the transformer 46 are 180° out of phase with respect to each other in order for this type of AC-bridge to function properly.

One signal goes via the circuit board 40 to the probe electrode 33, while the other goes through a variable resistor-capacitor network 47 on the circuit board 40. The length of lead from point a to point b on FIG. 4 is identical to the length of lead from point c to point d. The network 47 comprises a varactor 48 and a MOSFET 50, to the electrode 35. The length of lead from point e to point F on FIG. 4 is identical to the length of lead from point G to point H. The MOSFET 500 is used to measure the variable resistance which is a function of D-C voltage. Varying the gate drive voltage of the MOSFET 50 by a computer-controlled D.C. bias power supply 51 in the above-ground circuit 43 causes the resistance between points A and B in FIG. 4 to vary. Varying the reverse bias voltage of the varactor 48 by a computer-controlled D.C. bias power supply 52 causes the capacitance between points A and B to vary. The varactor 48 is used to vary the capacitance and to measure the soil capacitance characteristics, which are related to the D-C voltage obtained by balancing the bridge. The variable-resistor capacitor network 47 is thus used to balance the capacitance and resistance developed between the probe electrodes 33 and 35 when a signal passes through them. A capacitance 53, preferably 0.01 μf, isolates the two D-C bias power supplies 51 and 52 from each other. When the resistor-capacitor network 47 is varied such that the detector 55 senses a 0 voltage level, the resistance across the MOSFET 50 is equal to the resistance across the probe electrodes 33 and 35, and the capacitance across the varactor 48 then equals the capacitance across the probe electrodes 33 and 35.

This application of an AC-bridge is dependent on the fact that the two signals produced by the transformer are 180° out of phase. Therefore, the lead lengths ab and cd must be identical as are the lead lengths eF and GH—all the way through a high-pass filter 54 in the circuit 43 to the input of a phase amplitude detector 55. If one length were longer or shorter, the unmatched impedance might cause a phase shift in one of the signals and also add an undesired capacitance, inductance as well as a resistance.

The high-pass filter 54 is used to pass the high frequencies and attenuate the low frequencies, because all that is wanted are the radio-frequencies generated by the oscillator 45. Also, this filter 54 will attenuate the high-order harmonics of the fundamental signal, because it is important to exclude false signals from the detector 55. This filter 54 is theoretically a notch filter, although in a prototype a high pass filter was found to be sufficient.

When the signal enters the detector 55, the phase and amplitude is determined. The amplitude of the signal is most important. The goal is to achieve a zero voltage signal at the input of the detector 55. If the detector 55 senses a signal of significant magnitude, an analog-to-digital converter 56 will digitally transmit this signal to a computer 57. The signal is sent digitally because the computer 57 can only understand digital signals. When the computer 57 is pre-programmed, it controls the DC-bias supplies 51 and 52 through a digital-to-analog converter 58, such that the detector 55 eventually sees a zero voltage signal. When the computer 57 sees that the voltage signal from the detector 55 is not zero, it will control the power supplies 51 and 52 so that the varactor 48 and MOSFET 50 change in capacitance and resistance, respectively. This change creates a new signal to the detector 55. This sequence is done constantly until a zero-voltage level is achieved at the detector 55.

The probe electrodes 33 and 35 thus transmit electrical signals (corresponding to capacitance and conductivity between the electrodes 33 and 35), to the circuit board 40, which is in the probe 30, and the output from the circuit board 40 then goes to the detection and control circuitry 43 at ground level. The detections and control analyzer 43 includes the high-pass filter 54, the phase-amplitude detector 55, the analog-to-digital converter 56, and the computer 57 which includes a display or printing portion for reading the magnitude of the signals, and the digital-to-analog converter 58—all of which are standard items. The computer 57 is provided with suitable software 59 for enabling calculation.

Figure 5:
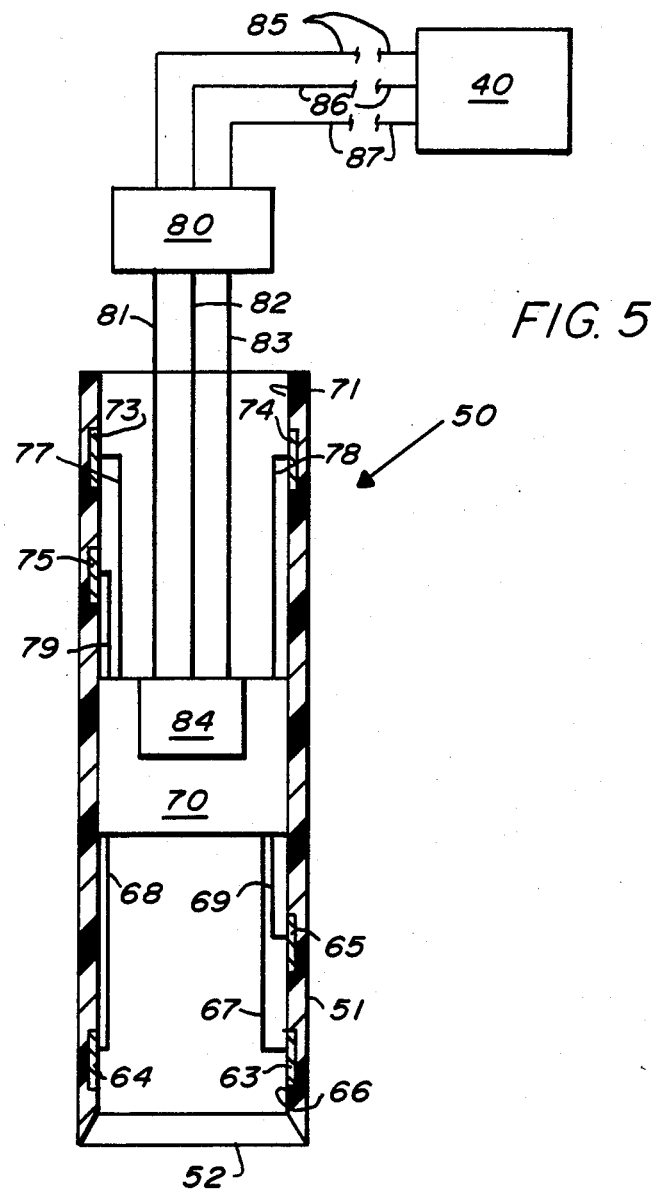
FIG. 5 is a view in elevation and in section of a modified form of probe of the present invention.
Figure 6:
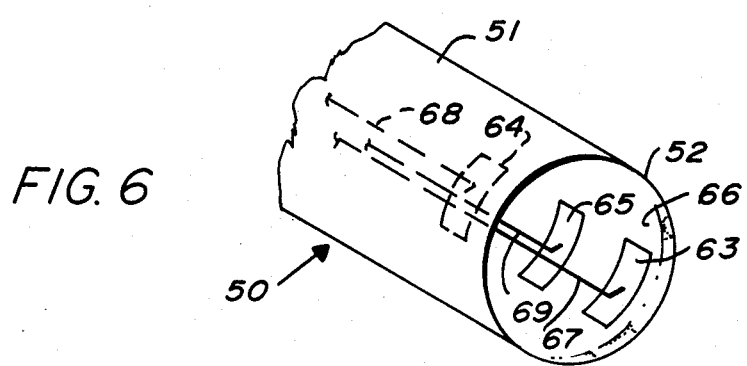
FIG. 6 is a fragmentary phantom view in perspective of the probe of FIG. 5.

A modified form of probe (FIGS. 5 and 6)

As shown in U.S. Pat. No. 4,219,776, it is often advisable to employ a three-electrode probe, in which two of the electrodes are on the same horizontal level and the third one is on a different level, vertically above one of the other two electrodes. This gives measurements along both vertical and horizontal axes. The measurements along the vertical axis can be as important as the measurements along the horizontal axis. Therefore this invention provides a modified form of probe 50 for three-electrode use.

The probe 60 has an insulating cylindrical shell 51, having a relatively thin or sharp bottom edge 52. There, or shortly above the edge 62, are two electrodes 63 and 64 on the same horizontal level. Vertically above one of the electrodes 63 is a third electrode 65. These electrodes 63, 64, and 65 are preferably located on the inner surface 66 of the shell 51 and are separated from each other by portions of the insulating shell 51. They may be curved sectors of about 90°, with the electrodes 63 and 64 located on opposite sides of the shell 51. They have respective leads 67, 68, and 69 extending up along the shell surface to a circuit board 70 generally like the circuit board 40, except that it must accommodate the two pairs of electrodes 63–64 and 63–65. The leads 67, 68, and 69 are identical in line impedance.

Above the circuit board 70 on the inside surface 71 of the tubular shell 51 are three mirror-image electrodes 73, 74, and 75 corresponding in positioning and in distance from the board 70 to the electrodes 63, 64, 65. They have respective leads 77, 78, and 79 identical in length to each other end, preferably, to the lengths of the leads 67, 68, and 69.

Finally, an above ground circuit 80 is connected to the circuit board 70 by leads 81, 82, and 83 to an oscillator 84 on the board 70, and by leads 85, 86, and 87 to a circuit corresponding to the circuit 40 that shown in FIG. 4, lead lengths again being identical.

Before using the probe 60, the circuit values of the electrodes 63, 64, and 65 are balanced in air to equal those of the electrodes 73, 74 and 75. This balance finally eliminates the line-impedance problem. The work in soil then continues with only the electrodes 63, 64, and 65 contacting the soil, and the procedure is the same as for FIG. 4 already described.

The importance of taking in situ measurements

With this simple system, in situ measurements can be taken, from which can be determined both the dielectric constant and conductivity between the electrodes 33 and 35. In some instances, both of these are determined and used, and in other instances a series of dielectric constants at different frequencies is sufficient. Thus, the electrical properties of soils can be measured in situ and almost instantaneously. These properties can then be interpreted to quantify the structure of particular soil systems, by which many mechanical properties can be determined. Moreover, the method is basically non-destructive, since there is no need to remove the soil or to treat it with anything, but only to probe it.

Heretofore, major difficulties in determining soil properties accurately, have arisen from disturbances during sampling and from the in situ use of penetrometers which altered the engineering properties of the soil.

The type of testing employed in the present invention has the advantage that the soil is tested in situ taking into account such factors as the environmental conditions which influence the engineering properties. Also, continuous data can be obtained through the profile, and the properties can be obtained in cases where obtaining undisturbed samples is very difficult, such as from water-saturated sands.

The present invention's use of in situ techniques with radio-frequency signals (FIGS. 7–10)

The present invention provides an non-destructive method of characterizing particular systems by considering the electrical properties of soils which can be determined in situ without significantly disturbing the soils.

The present invention applies to the electrodes a radio-frequency alternating electrical field.

For example, in the case of sands or granular systems, both the dielectric constant $\epsilon$ and the conductivity $\sigma$ remain constant throughout a wide range of radio frequencies, as is shown by FIG. 7. In contrast, the dielectric constants $\epsilon$ and conductivity $\sigma$ values do not remain constant at various frequencies for cohesive soils, as is shown in FIG. 8.

The principal factors influencing the electrical dispersion of fine grained soils in the radio-frequency range, of about 1 MHz to 100 MHz, are the compositional properties of the different soil phases and the heterogeneous nature of the soil system.

Figure 9:
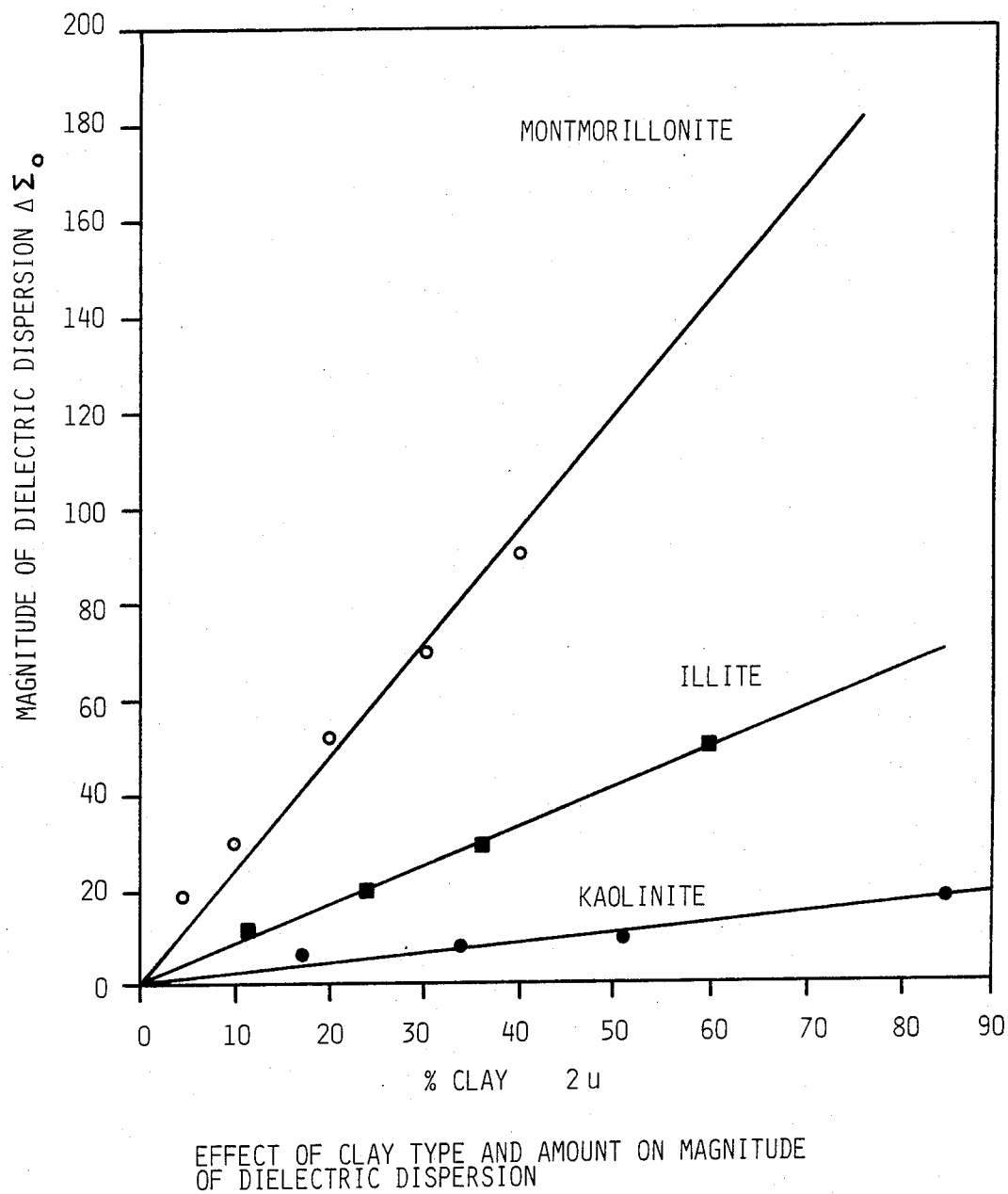
FIG. 9 is a graph showing the correlation between the magnitude of the dielectric dispersion $\Delta\epsilon_0$ and the clay fraction in a soil, plotting the dielectric dispersion against the percent of clay in each of several samples.

The difference between the maximum and minimum values of the dielectric constant $\epsilon$ in the radio-frequency range may be defined as the magnitude of dielectric dispersion $\Delta\epsilon_0$. FIG 9, plotting the magnitude of dielectric dispersion $\Delta\epsilon_0$ against the percent of clay in some test soils, illustrates that each of these clays has a different slope but that each follows a basically linear pattern. Each clay has a different magnitude of dielectric dispersion $\Delta\epsilon_0$.

I have discovered, as shown in FIG. 10, that when various magnitudes of dielectric dispersion are plotted against the specific surface area of the soil particles in the different clays, obtained in a conventional manner the result is a single linear graph. This important fact gives a method for rapidly determining the specific surface area of the particles in a clay soil, for the magntidue of dielectric dispersion have only to be obtained and the graph of FIG. 10 gives the specific surface area.

Applications of the magnitude of dielectric dispersion: the formation factor, anisotrophy index and shape factor From the low frequency conductivity measurements at or near 1 KHz, the formation factor F is defined as the ratio of the pore fluid conductivity, $\sigma_s$ to the soil sample conductivity $\sigma$ as follows, $F=\sigma_s/\sigma$. Elsewhere, it has been shown that the formation factor F relates to the porosity and anisotropy of sand particles. See my earlier U.S. Pat. No. 4,219,776. The formation factor F was there shown to be a tensorial parameter with tensorial components related to the microstructural features in sands. The average formation factor $\overline{F}$ and the anisotropy index A are defined for a transversely isotropic soil as follows:

$$F=(F_V+2F_H)/3,$$

and $$A^2 = F_V/F_H,$$

where $F_V$ is the formation factor in the vertical direction and $F_H$ the formation factor in the horizontal direction. An integration technique derives an expression for average formation factor $\bar{F}$ as a function of porosity n and average shape factor $\bar{f}$ as $\bar{F} = n^{-\bar{f}}$.

The average shape factor $\bar{f}$ is a negative slope of the log $\bar{F}$-log n plot. It is the first invariant of the second order shape factor tensor f, and it relates the electric fields inside and outside the sand particles. It has been shown both theoretically and experimentally that the shape factor is direction dependent, and depends on porosity, gradation, and the shape and orientation of the particles. Since the average formation factor $\bar{F}$ is independent of the orientation of the particles, the average shape factor f for a given sand is a function of porosity and the shape of the particles.

The electrical parameters $\bar{F}$, A, and $\bar{f}$ of sand deposits are governed by the grain and aggregate characteristics of the particles. Since $\bar{F}$ is a unique function of porosity, since A quantifies the orientation of the particles, and since $\bar{f}$ is a measure of the shape of particles, $\bar{F}$ and A may be used to quantify the aggregate property. The aggregate property is sensitive to sampling disturbance and needs to be measured in situ. Grain property (shape) is insensitive to sampling disturbance, and can be determined on disturbed samples. It is therefore possible to correlate certain soil properties, such as liquefaction potential, friction angle, permeability, and compressibility, with the combination of the parameters $\bar{F}$, A, and $\bar{f}$. Empirical correlations of this type are extremely useful in evaluating the performance of sites which contain sand deposits.

Intercluster and intracluster void ratios

Variation of the soil conductivity and dielectric constant of the soil can be used to quantify and the intercluster and intracluster void ratios of cohesive soils. The concept that the primary soil particles exist in clusters in fine-grained soils has been utilized heretofore in deriving theoretical dispersion relationships. According to this concept a particulate system is considered to have clusters, primary particles plus intercluster pores, and intra cluster pores. The total current through a soil sample may be considered as having three components: (1) a current through intercluster solutions of clusters in series, (2) a current through clusters in contact with each other, and (3) a current through intercluster solution only. The apparent dielectric constant $\epsilon'$ and the apparent conductivity $\sigma'$ for the model can thus be evaluated by elementary electrical network analysis. The inter- and intra-cluster void ratios $e_p$ and $e_1$ have been expressed in terms of the three-element electrical model parameters by relating the cluster model to the electrical model. The detailed derivation of the three element models and inter- and intra-cluster void ratios from model parameters have been worked out by a computer optimization method. Applying this method to the electrical dispersion characteristics the intercluster and intracluster void ratios can be quantified. The significance of this quantification of intercluster and intracluster void ratios is that the swelling index $\kappa$ can be predicted from in situ measurements of dielectric dispersion. See FIG. 14 and the discussion below. This value of $\kappa$ is necessary for use in situ prediction of the stress-strain behavior of soils.

Useful parameters

The parameters utilized in developing the nondestructive method of characterizing the behavior of fine grain soils are: $\bar{f}$, $\bar{F}$, A, $e_1$, $e_p$, and $\Delta\epsilon_0$. Based on the mechanisms controlling different aspects of the mechanical behavior of soil, and the factors influencing the electrical parameters, appropriate correlation exists between the electrical parameters and the mechanical parameters $\lambda$, $\chi$, and M.

Figure 12:
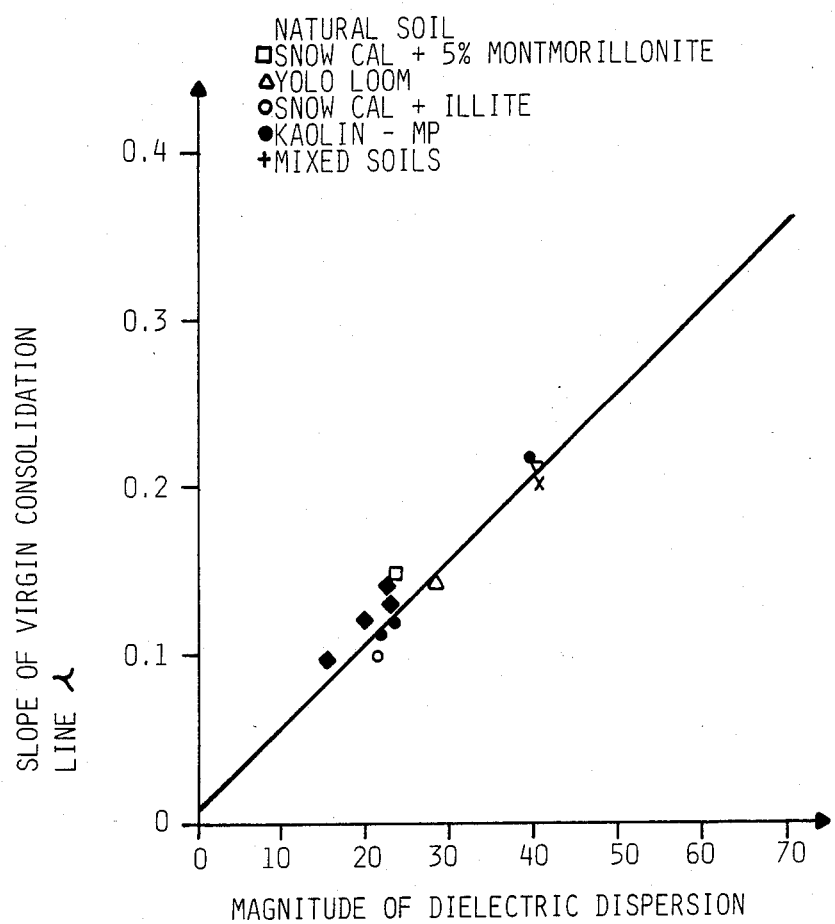
FIG. 12 is a graph plotting the slope of the virgin consolidation line (or compression index line) $\lambda$ against the magnitude of dielectric dispersion $\Delta\epsilon_0$, showing data from several different types of soil.

Compression line index (FIG. 12)

The slope of the compression index line $\lambda$, also known as the isotropic consolidation line, can be obtained from the relation shown in FIG. 12, where the slope of the virgin consolidation line $\lambda$ is plotted against the magnitude of dielectric dispersion $\Delta\epsilon_0$ for several different types of soils. The factors influencing the magnitude of dielectric dispersion $\Delta\epsilon_0$, when investigated by the present inventor, led to the discovery that $\Delta\epsilon_0$ was significantly influenced by the type and amount of clay mineral. The values of $\Delta\epsilon_0$ were shown to increase in the sequence kaolinite < illite < montmorillonite. The compression index of the soils also increases in the same sequence. The magnitude of dispersion $\Delta\epsilon_0$ decreases with an increase in the percentage of sand in sand-clay mixtures, and so does the compression index $\lambda$. It has been shown by others that the compression index of kaolinite is decreased when the electrolyte concentration is increases from 0.0001N sodium, to 1.0N sodium, and the present inventor has shown that $\Delta\epsilon_0$ also decreases with increasing electrolyte concentration.

Since, the factors influencing the mechanisms controlling the compression of clays and the magnitude of dielectric dispersion are the same, it is possible to correlate $\Delta\epsilon_0$ with $\lambda$, and it is found that this is a linear relationship for natural clays.

The value of $\lambda$ is necessary for the prediction of the stress-strain behavior of soils in situ, and the settling of structures.

Figure 13:
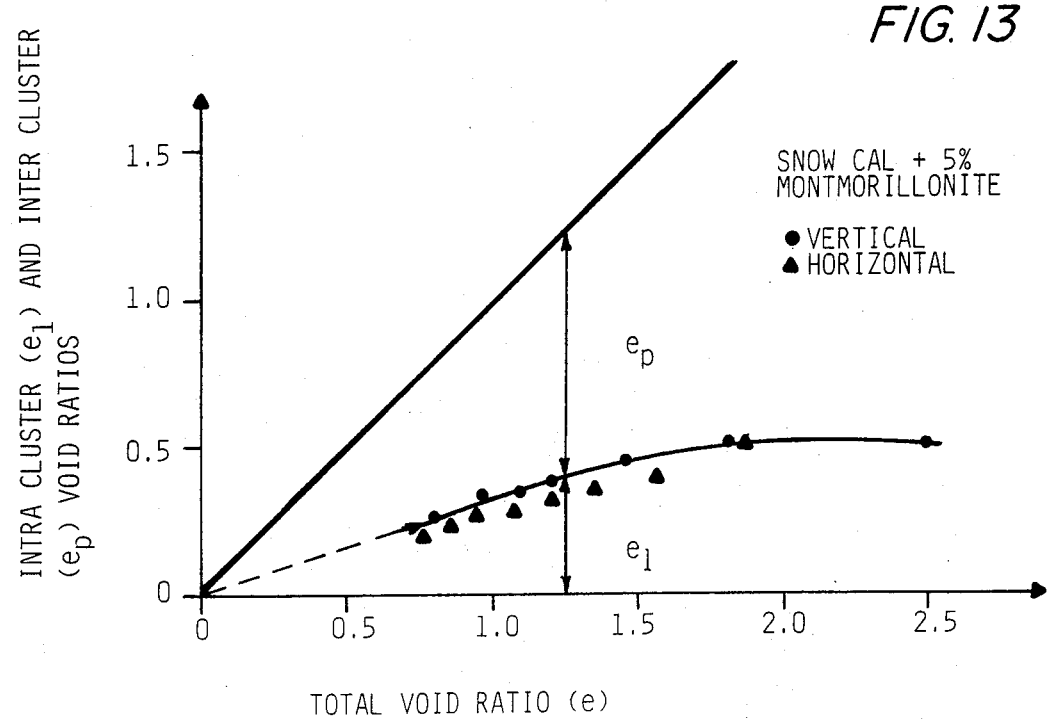
FIG. 13 is a graph plotting the intercluster and intracluster void ratios $e_1$ and $e_p$ against the total void ratio e.

The slope of the isotropic swelling line $\kappa$ (FIG. 13)

The swelling characteristic of saturated clays due to the removal of external load has been investigated widely, but heretofore explanation of the mechanism controlling swelling characteristics was not very practical because of the complicated structural arrangements of particles in the clays.

FIG. 13 plots the intracluster and intercluster void ratios against the total void ratio. It shows the variation of the intracluster $e_1$ and intercluster $e_p$ void ratios with the total void ratio evaluated, using electrical dispersion data for Snow Cal sand (95%) plus montmorillonite clay (5%). Measurements made in both the vertical and horizontal directions give identical results. It has heretofore been shown that the swelling of fine grained soils is caused by the swelling of clusters, and that the decrease in intercluster pores during compression is irreversible.

Figure 14:
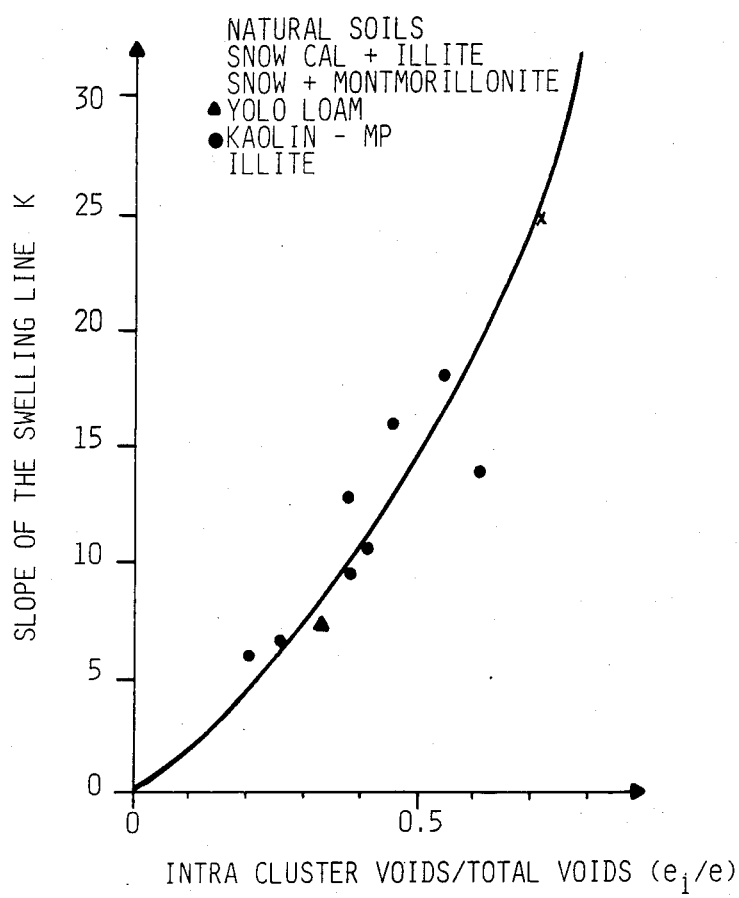
FIG. 14 is a graph showing the correlation between the slope of the isotropic swelling line $\kappa$ and the ratio of the intercluster-to-total void ratio $e_1/e$.

If the ratio of intracluster void ratio to total void ratio is large for a given soil, the elastic compression due to an increase in the external load would be high; consequently, swelling would also be high when the load is removed. Assuming this mechanism of swelling, the ratio $e_1/e$ is correlated with $\kappa$ as shown in FIG. 14. This is, as noted above, necessary for the prediction of the in situ stress-strain behavior.

Figure 15:
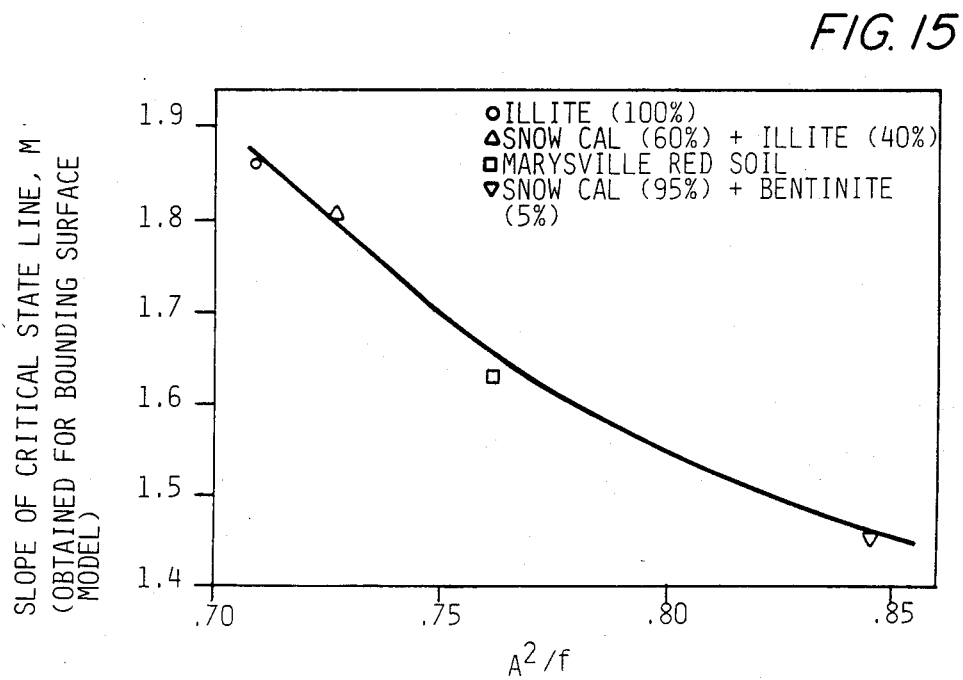
FIG. 15 is a graph showing the correlation between the slope of the critical state line M in the bounding surface plasticity theory and a certain electrical parameter, $A^2/\hat{f}$, where A is the anisotropy index and $\hat{f}$ the shape factor.

The slope of the critical state line M of the bounding surface theory (FIG. 15)

When a soil element is sheared under either drained or undrained conditions, experimental results indicate that the soil element fails when the stress path reaches a critical state line, independent of the initial stress state of the soil element. At failure, the void ratio e and the effective mean normal pressure p lie on a unique line referred to as a critical state line M on the e-p space. This is known as the critical state concept. The slope of the critical state line M represents the ultimate shear strength of the soil. The components of ultimate shear resistance, and hence the value of M, depend on many factors such as particle size, shape, surface texture, and the structure of the soils resulting from the attractive and repulsive forces between the adjacent clay particles.

However, the present invention includes the discovery that M can be correlated with an electrical index defined as a function of A and $\bar{f}$. Values of M were obtained by matching theoretical and experimental stress-strain relationships, and a direct assessment from the failure value of q/p could only be approximate, because of the inaccuracies in measurement of the stress parameters at large strain, and therefore would underestimate M, because the failure intervenes before the critical state line. The correlation between M and $A^2/\bar{f}$ is based on results corresponding to four different soils tested, as shown in FIG. 15. A reasonable non-linear correlation between M and $A^2/\bar{f}$ is evident from this view. This is needed for the prediction of in situ stress-strain behavior.

All three parameters $\lambda$, $\kappa$ and M are predictable from the electrical properties and can be directly used in a bounding surface plasticity model to predict the in situ stress-strain relationship of cohesive soils. For example, the deformation behavior of soils is required in any geotechnical engineering problem such as slope stability, levels that formulations can sustain, and so on.

Dielectric conductivity cone penetrometer use for soil profiling and hydrocarbon detection The application of cone penetrometers for soil profiling and soil investigation has been described in various publications. The cone penetrometer method of soil classification provides an index dependent upon the test method. The three major contributing factors are (1) equipment and procedure, (2) penetration mechanics and layered media, and (3) soil composition and environment. Because of these factors influencing a cone penetrometer log, it is difficult to obtain in all cases an index of even only those soils in the immediate vicinity surrounding the tip.

A method of classifying soils in the immediate vicinity surrounding the cone tip, according to the present invention, utilizes the dielectric conductivity obtained. The method is based on the dielectric dispersion characteristics of soil, as described above. The method depends only on the soil composition and the environmental factors.

It is then possible to classify continuously a soil as the dielectric cone penetrometer is pushed into the soil. The magnitude of dielectric dispersion can be measured and gives information about the specific surface, or soil type. The water content of the soil can also be predicted using the dielectric constant at frequencies greater than 30 MHz. The method is independent of the equipment and of the procedure, and is independent of the penetration mechanism of the layered media. It measures only the soil composition and does so in a more fundamental manner than did previous methods.

Figure 16:
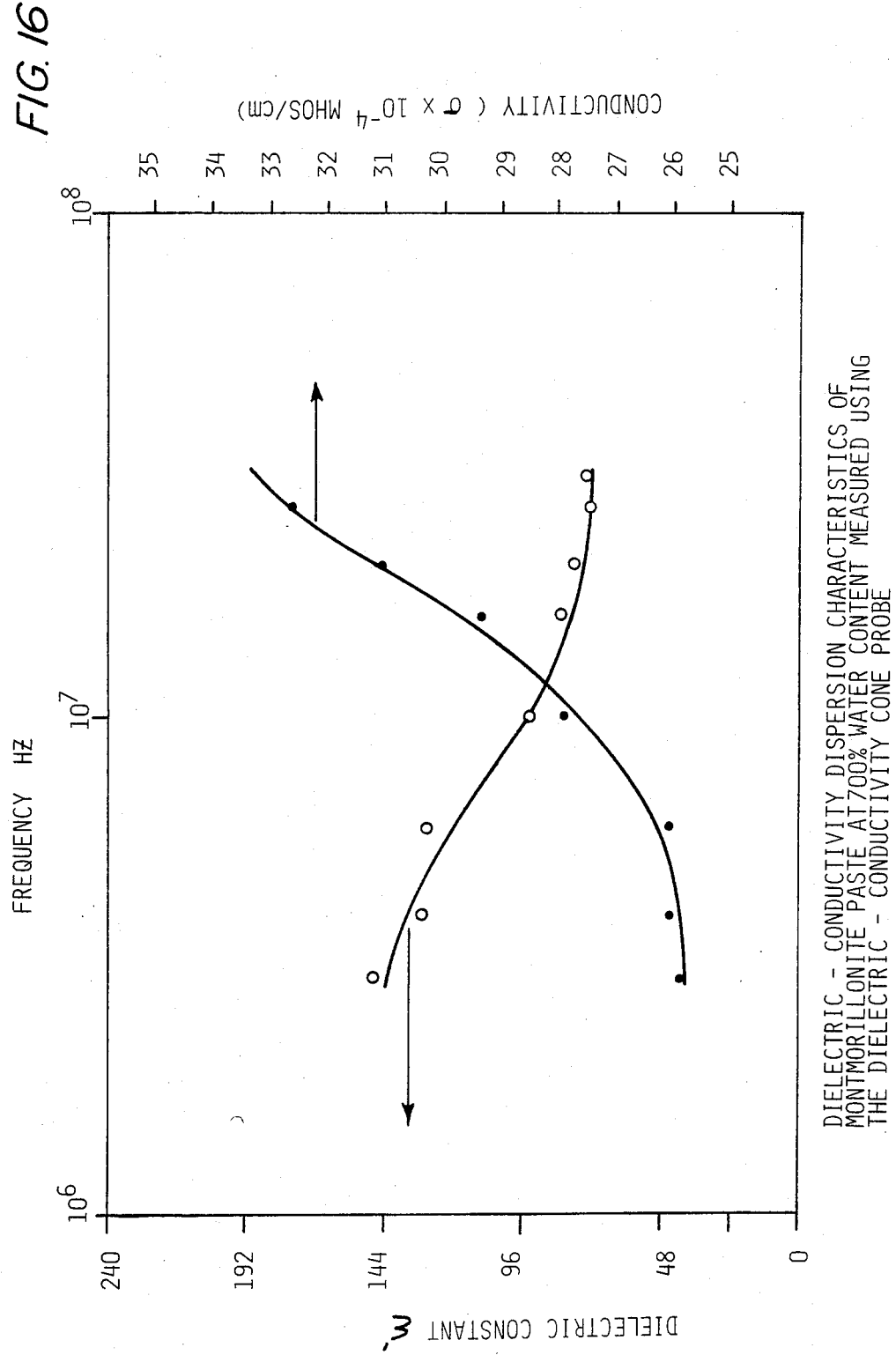
FIG. 16 is a graph of the dielectric and conductivity characteristics at various frequencies of a highly swelling clay with a very high water content.

Thus, FIG. 16 shows the dielectric and conductivity dispersion characteristics of a montmorilonite paste at 700% water content, measured by the dielectric-conductivity cone probe of this invention. The curves are quite characteristic.

Figure 17:
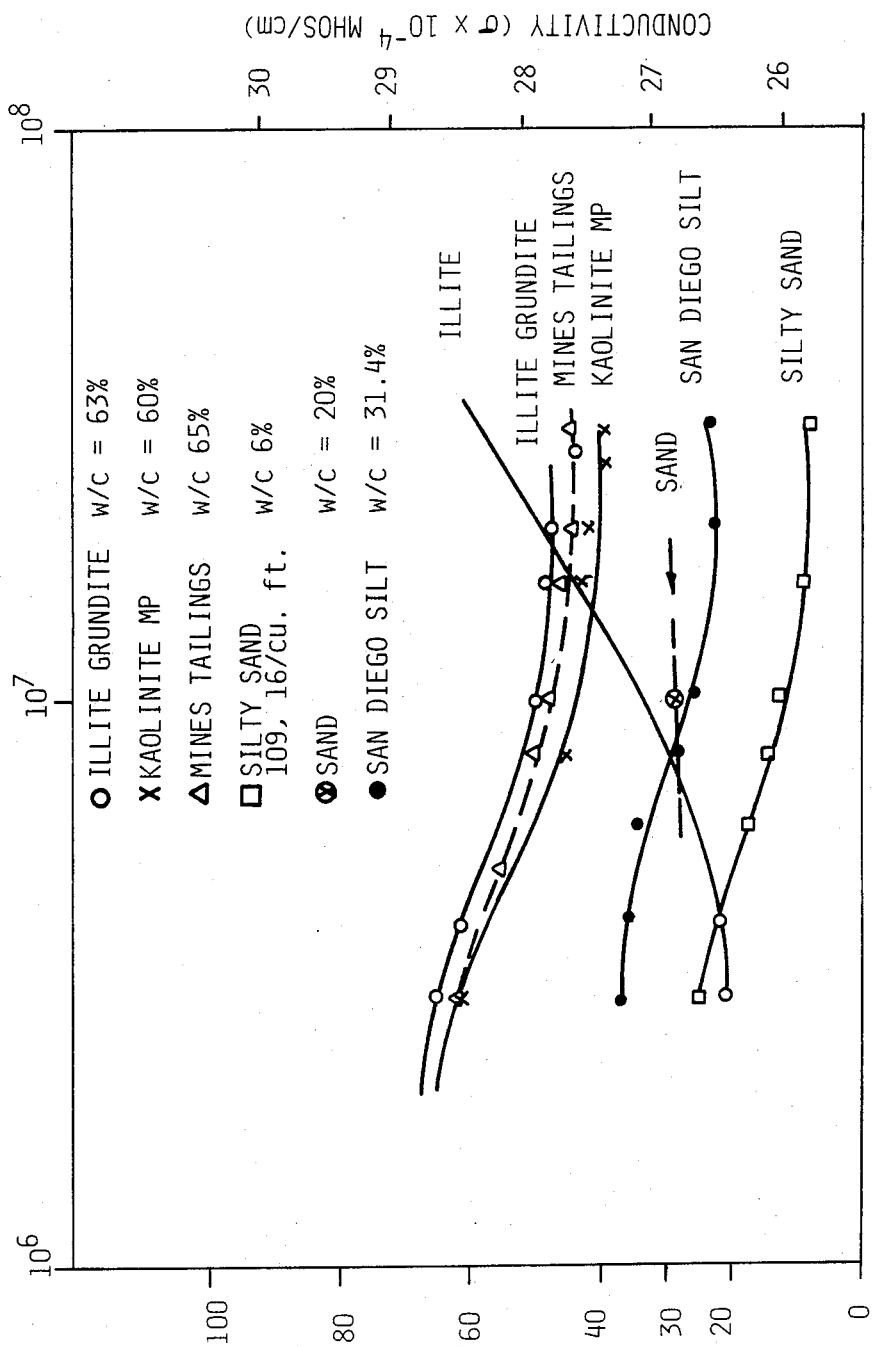
FIG. 17 is a similar graph of a series of clays, silts, and sand with high water content.

Similarly, FIG. 17 shows dielectric-conductivity data from a variety of soils, namely (1) illite grundite with a water content of 63%, (2) kaolinite MP with a water content of 60%, (3) mines tailings with a water content of 65%, (4) silty sand with a water content of 6%, (5) sand with a water content of 20%, and (6) San Diego silt with a water content of 31%. Each of these has a characteristic curve, and the effect of water content is clearly shown.

Applicability of the method to hydrocarbon detection

The dielectric dispersion characteristics of soil in a soil-water mixture are different from those of a soil-water-hydrocarbon mixture.

Figure 18:
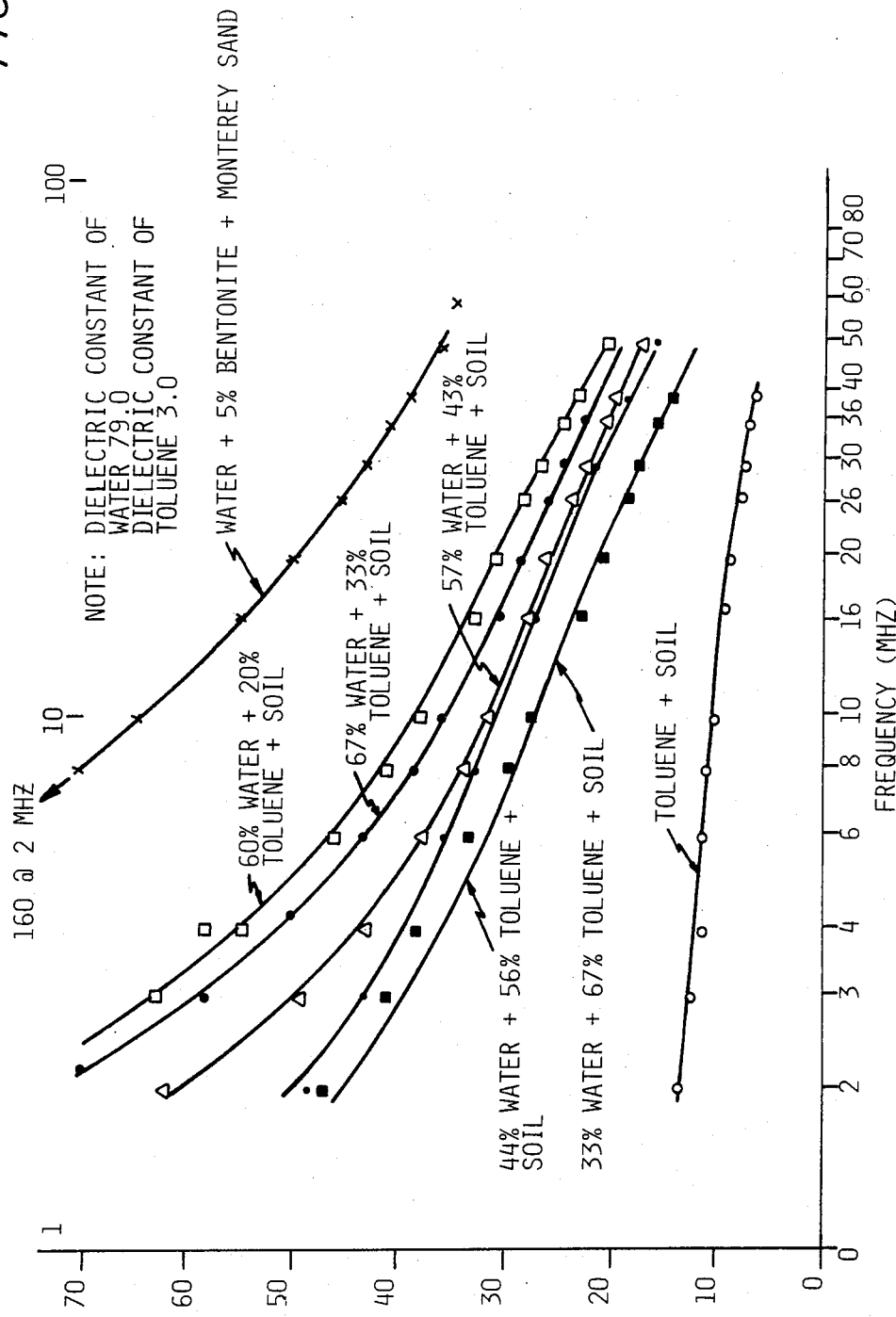
FIG. 18 is a graph of electrical dispersion data for a mixture of 5% bentonite and 95% Monterey sand, containing different percentages of toluene and of water, plotting dielectric constant against frequency.

When an electrical impulse in the form of a radio-frequency alternating current field is applied to a soil-water-electrolyte system, or to a soil-water-hydrocarbon-electrolyte system, a response is produced which can be measured in terms of two electrical properties, namely, the apparent dielectric constant $\epsilon'$ and the conductivity $\sigma$. When the $\epsilon'$ and $\sigma$ values of any particulate system are measured as a function of frequency, $\epsilon'$ and $\sigma$ values are independent of the frequency in granular soils (see FIG. 7), but in the case of cohesive soils (see FIG. 8) the value of $\epsilon'$ decreases and the value of $\sigma$ increases as a function of the frequency of the alternating current field, in other words, the greater the frequency, the lower the dielectric constant and the greater the conductivity. When the percentage of hydrocarbons is changed in a system exhibiting dielectric dispersion characteristic, the dielectric constant values also change as a function of frequency, as shown in FIG. 18, where the different curves represent a single synthetic soil—a mixture of 5% bentonite and 95% Monterey sand—but with different percentages of the hydrocarbon toluene and of water. Toluene is not much different, in the pertinent characteristics concerned here, from other hydrocarbons, such as gasoline.

Conductivity measurements are insensitive to detect oil spillage.

Dielectric constant measurements at 30 MHz are very sensitive to replacement of water by oil. There is an abnormal decrease in dielectric constant after oil seepage.

As stated, measurement of conductivity or of dielectric constant at one frequency cannot quantify soil type and hence is inadequate to quantify hydrocarbon content or to classify soils. Yet electrical conductivity and dielectric constant measurement at one frequency have been the common methods to identify the presence of hydrocarbon.

This invention includes the discovery that the measurement of dielectric constant as a function of frequency makes is possible to quantify the type of soil and take into consideration the effect of pore fluid composition.

One is then left with the variables of water saturation, the amount of air, and the amount of hydrocarbon. When one considers a system saturated with water and hydrocarbon, the only two variables to consider are the water saturation and the hydrocarbon in different types of saturated soils by considering the dielectric dispersion characteristics.

From a series of readings at different frequencies one can determine the type of soil, the water saturation and the amount of hydrocarbon. A knowledge of the soil type and water saturation is necessary to predict the amount of hydrocarbon in any medium.

The dielectric probe and probe circuit of FIGS. 1-4 enables the application of the dielectric conductivity dispersion characteristics to soil profiling and hydrocarbon detection during field exploration. Measurements of the capacitance and resistance are obtained by using the R-C network 47 as shown in FIG. 4, having the varactor 48 and the MOSFET 50 in conjunction with the probe 30. These measurements show in FIG. 19 that the dielectric constant and conductivity values are independent of frequency in salt water samples of different conductivity and in glycerine. Dielectric dispersion data obtained on several saturated soils using a laboratory model of the field probe, are shown in FIG. 10.

Figure 20:
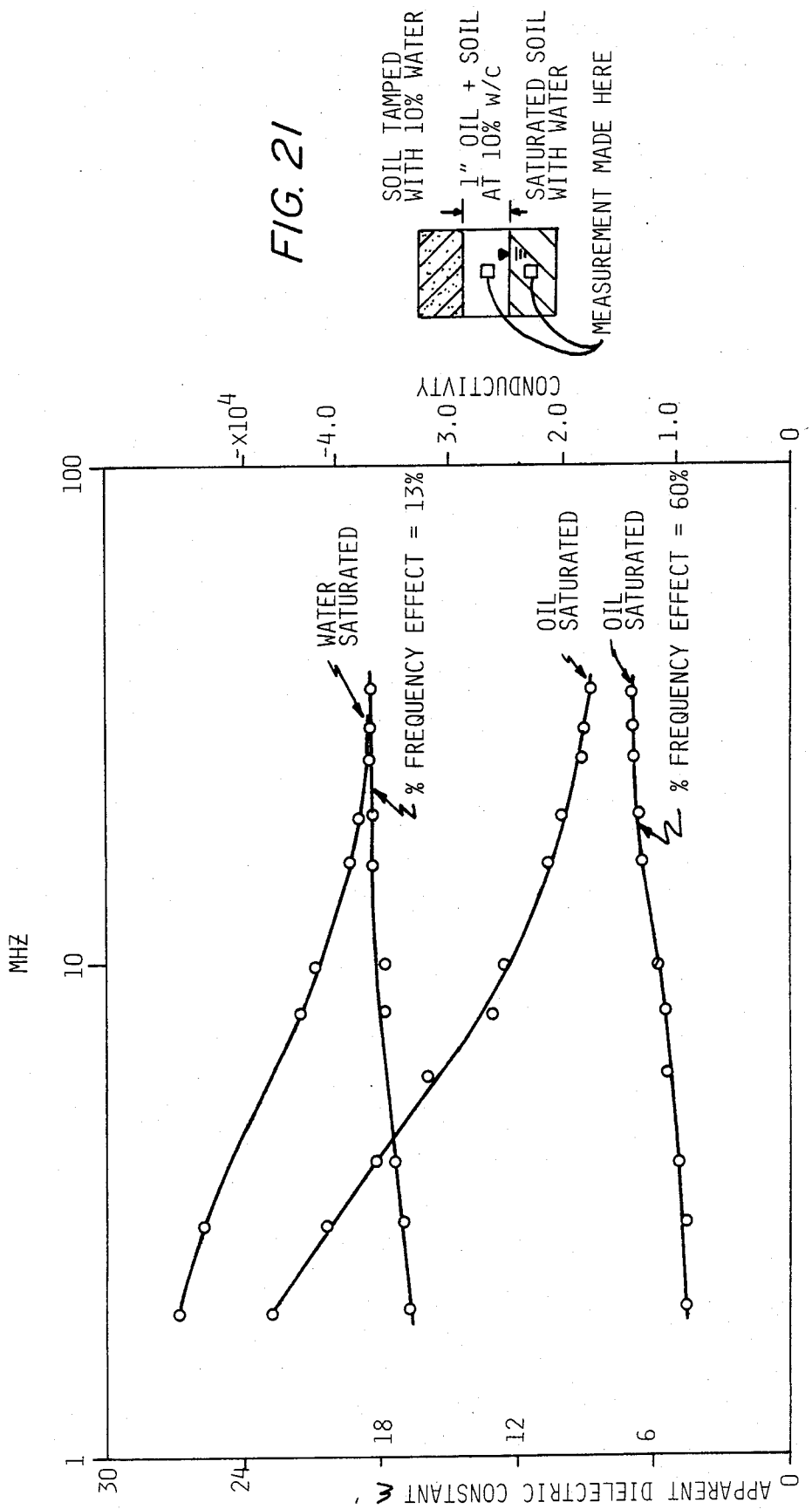
FIG. 20 is a similar graph of similar measurements for sandy silt having in some instances water saturations and in others oil saturation, showing the difference in dielectric dispersion between water-saturated sandy silt and oil-saturated sandy silt.

A comparison of $\epsilon'$ and $\therefore$ versus frequency relationships obtained on a water-sandy silt mixture and a water-oil sandy silt mixture, is shown in FIG. 20.

Figure 21:
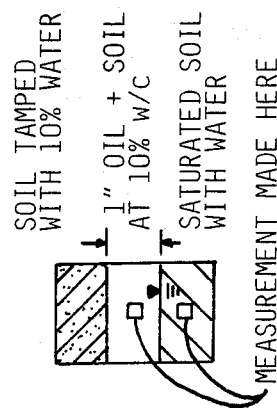
FIG. 21 is a diagram for the soil strata measured in FIG. 20.

These measurements were made in soil strata like those shown in an insert, FIG. 21. At the bottom is a layer of the soil saturated with water. Above that is a layer of oil-saturated soil containing 10% water. Above that is tamped soil with only 10% water.

The variation of the dielectric dispersion data as the cone probe 30 is pushed into a plastic cylinder containing sandy silt material, existing at different states of water and oil saturation is shown in FIG. 22, with FIG. 23 showing that the soil strata are, beginning at the top, (1) a layer of soil with 10% water content, (2) soil with the same water content through which oil has seeped, (3) soil like that of (2) at a lower level, and (4) the same soil saturated with oil.

The evaluation of the presence of hydrocarbons in a water-oil saturated porous medium is a simpler task than that in a water-air-oil saturated system. The mechanism causing an increase in dielectric constant in a soil-water-air system when hydrocarbon spillage occurs is due to the displacement of air by the hydrocarbon.

The method involves the above-explained determination of the electrical dispersion characteristics of the soil. A granular medium exhibits no electrical dispersion (FIG. 7), whereas a cohesive medium exhibits electrical dispersion characteristics (FIG. 8). In an electrically dispersive soil system, when the dielectric constant at 30 MHz is plotted against water saturation (Se/1+e) where S is the degree of saturation and e is the void ratio, a linear relationship is observed. This relationship defines the in situ state of the soil.

A decrease in dielectric constant at a given water saturation is observed when the water is displaced by oil. Thus, it is possible to detect oil spillage and the presence of hydrocarbons if measurements of dielectric constants are made.

While the conductivity at any particular frequency changes with water saturation for different mixtures of soil-air-water and hydrocarbon percentages, the conductivity decreasing with a decrease in water saturation, there is no systematic difference in conducitivity for a soil-air-water mixture and soil-air-hydrocarbon-water mixture at a given water saturation percentage. Conductivity appears to be an insensitive parameter to detect oil spillage.

In a dry soil there is an increase in dielectric constant when the air is replaced by the hydrocarbon.

An alternate method of presenting the results is to examine the variation of dielectric constant and conductivity as a function of oil and water saturations, V. The value of $V = e - e_a/e$, where e is the total void ratio and $e_a$ is the void ratio of air.

The variation of dielectric constant at 30 MHz with oil water ratio for saturated silty sand is significant. Saturation in this case refers to the voids being filled with water and oil. This relationship can be used to quantify the amount of hydrocarbon present in a saturated silty sand.

Thus, dielectric dispersion characteristics can be used to characterize soils in their in situ state. There is an increase in the dielectric constant at 30 MHz when the air is replaced by hydrocarbon at a given water saturation. There is a decrease in dielectric constant when water is replaced by oil, as indicated by the results obtained with a prototype in situ probe.

Hydrocarbon content compared with ice content at various percentages of melting The dielectric constants of hydrocarbons and ice are in the order of 1-3. A sand at a porosity of 0.45 has a dielectric constant of about 30. The same sand saturated with hydrocarbon would exhibit a dielectric constant of about 5. In a similar manner, the dielectric constant of ice is in the order of 3. Depending on the degrees of melting, water-ice mixtures exhibit a dielectric constant varying from 3 to 80.

Other soil features different soils at different porosities exhibit a dielectric constant variation at frequencies greater than 30 MHz from about 5 to 75, thereby enabling the prediction of porosity.

Depending on their specific surface area, soils exhibit a change in dielectric constant of 10 to over 100 when the frequency is changed from 1 MHz to 50 MHz. The specific surface area is uniquely related to soil type (e.g. clay, silt or sand).

The dielectric constants are measurable in situ by the dielectric-conductivity probe of this invention. This tool enables the measurement of hydrocarbon content, ice content, porosity, type of soil characterized in terms of specific surface area and hazardous waste content when present in reasonable amounts.

The probe can be used to obtain a large quantity of in situ tests data in a short time. The probe can be attached to standard cone penetration rods and jacking equipment. At it is jacked into the ground a continuous computer readout provides the data required to detect ice, hydrocarbon, water table and hazardous waste. The soil type and density can also be measured very quickly and economically. Relatively thin seams of soil, ice or hydrocarbon can be distinguished. Moreover, the probe provides a cost effective alternative to slow and expensive drilling and sampling methods.

Figure 24:
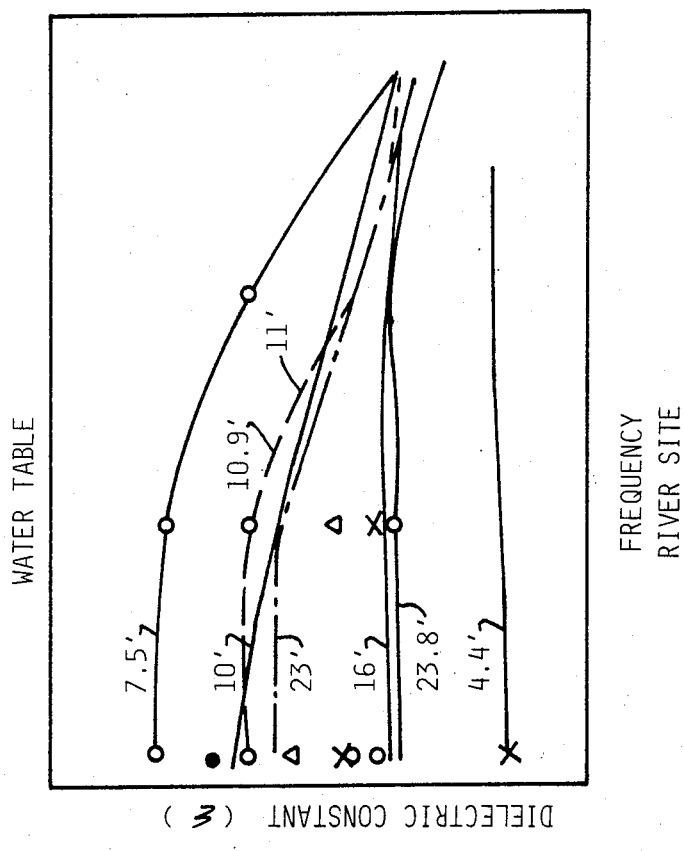
FIG. 24 is a graph showing test results obtained at a river site in Long Beach, Calif., using method and apparatus of this invention.

For example, FIG. 24 shows test results obtained at a river site in Long Beach, analyzed to obtain the main characteristics of the soil at the site. A comparison of these results with cone penetration data showed a reasonably close agreement.

The variation of dielectric constant and conductivity as a function of frequency in the radio frequency range is a method of characterization of the composition and structure of particulate systems. The electrical dispersions, i.e., the variation of dielectric constant, are conductivity as a function of frequency and when suitably interpreted can be used to quantify the composition and structure of particulate systems and can also be related to mechanical properties and to detect hydrocarbon, hazardous waste, different degrees of melting ice, and any system where the electrical properties of the systems consisting of different components are different.

There are several ways of making the electrical measurements as a function of frequency, one method having been given here.

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. A soil probe system comprising
   a hollow, tubular cylindrical member made of insulating material, for penetrating soil in a direction along the axis of said cylindrical member, said member having a lower end which first enters the soil during penetration,
   three soil-contacting electrically conductive electrodes adjacent to the lower end of said cylindrical member, two on the same horizontal level and one spaced thereabove, said electrodes being mounted in said cylindrical member a short distance above its lower end,
   an electrical-electronic measuring system for measuring soil capacitance, connected to said electrodes by conducting means providing identical line impedance from each electrode, said measuring system having an initial electronic portion inside said cylindrical member and close to said electrodes so as to minimize line impedance, the line impedances of each electrode and said initial portion being identical, said initial portion supplying electrical voltages at radio frequencies to said electrodes and receiving electrical signals from said electrodes and having means for generating related electronic signals,
   a second portion of said measuring system distant from said cylindrical member and connected thereto by lines having identical line impedance, for sending signals at a wide range of radio frequencies to said initial portion, whence they go to said electrodes; and for receiving said electronic signals from said initial portion and manipulating them electronically to produce data output,
   the lines connecting the electrodes to the initial portion being of identical length and type for each electrode and the lines connecting the second portion to said initial portion being of identical length and type,
   three other electrodes mounted in said cylindrical member above said initial electronic portion in mirror-image relation to sid soil-contacting electrodes and connected to said initial portion by lines having identical line impedance to the lines connecting said initial portion to said soil-contacting electrodes, and means for balancing in air said three soil-contacting electrodes with said three other electrodes.

2. A soil probe system, comprising
   a hollow, tubular cylindrical member made of insulating material, for penetrating soil in a direction along the axis of said cylindrical member, said member having a lower end that first enters the soil during penetration,
   at least two electrically conductive electrodes mounted in said cylindrical member a short distance above its lower end, and
   an electrical-electronic measuring system connected to said electrodes by conducting means providing identical line impedance from each electrode,
   said electrical-electronic measuring system comprising
   an initial electronic portion of said measuring system inside said tubular cylindrical portion and close to said electrodes so as to minimize line impedance, said initial portion including a resistance, capacitance network supplied with one D-C bias voltage for said resistance and another D-C bias voltage for said capacitance, said network having means for varying the resistance and the capacitance,
   said measuring system also having a second portion distant from said cylindrical portion and connected to said initial electronic portion by lines having identical line impedance, for supplying radio frequency signals 180° out-of-phase with each other to said network, for receiving said electronic signals, and for manipulating them electronically to produce data output, said second portion including an oscillator supplying radio-frequency signals to said electrodes and to said network, a phase amplitude detector connected to said lines, and computer means connected to said detector for controlling the variation of resistance and capacitance in said network to obtain balance in said bias voltages to preserve the 180° phase difference.

3. The probe system of claim 2 including means for applying from said oscillator a plurality of different known frequencies of radio-frequency current to said electrodes, for enabling the accurate determination of soil capacitance at said different frequencies.

4. The probe system of claim 3 having means in said second circuit portion for determining from the soil capacitance the dielectric dispersion characteristics of said soil.

5. A soil probe system, comprising
   a hollow, tubular cylindrical member terminating at its lower end in a conical portion, said member being made of insulating material, and used for penetrating soil along the axis of said member with said conical portion penetrating first,
   a pair of metal, electrically conductive, ring electrodes mounted in said cylindrical member a short distance above said conical portion, said ring electrodes lying flush with the outer surface of said cylindrical member and contacting said soil during said penetration and spaced apart from each other by said insulating material, and
   an electrical-electronic measuring system connected to said electrodes by conducting means providing identical line impedance for each ring,
   said electrical-electronic measuring system comprising
   an initial electronic portion of said measuring system inside said tubular cylindrical portion and close to said electrodes so as to minimize line impedance, said initial portion including a resistance-capacitance network supplied with one D-C bias voltage for said resistance and another D-C bias voltage for said capacitance, said network having means for varying said resistance and capacitance therein, said measuring system also having a second portion distant from said cylindrical portion and connected to said initial electronic portion by lines having identical line impedance, for receiving said electronic signals and manipulating them electrically to produce data output, said second portion including an oscillator supplying radio-frequency signals to said electrodes, said signals being 180° out-of-phase, a phase amplitude detector connected to said lines, and computer means connected to said detector for controlling the variation of resistance and capacitance in said network to obtain balance in said bias voltages to preserve the 180° phase difference.

6. The probe system of claim 5 including means for applying from said oscillator a plurality of different known frequencies of radio-frequency current to said electrodes, for enabling the accurate determination of soil capacitance at said different frequencies.

7. The probe system of claim 6 having means in said second circuit portion for determining from the soil capacitance the dielectric dispersion characteristics of said soil.

8. A soil probe system, comprising a probe member for said penetration having a tubular cylindrical portion made of insulating material and terminating at its lower end in a metal conical portion which first penetrates the soil, said member penetrating the soil along the cylindrical axis of said member, a pair of soil-contacting metal, electrically conductive, ring electrodes mounted in said cylindrical portion a short distance above said conical portion, the outer surfaces of said ring electrodes lying flush with the outer surface of the cylindrical portion and spaced apart from each other by said insulating material of said cylindrical portion, and an electrical-electronic measuring system connected to said electrodes by conducting means providing identical line impedances between each ring and said system, said measuring system having an initial electronic portion inside said tubular cylindrical portion and close to said electrodes so as to minimize line impedance, said initial portion including a resistance-capacitance network connected to one said electrode and supplied with one D-C bias power supply for said resistance and another D-C bias power supply for said capacitance, said network having means for varying the resistance and the capacitance therein, said measuring system also having a second portion distant from said cylindrical portion and connected to said initial electronic portion by lines having identical line impedance, for receiving said electronic signals and manipulating them electronically to produce data output, said second portion including an oscillator supplying radio-frequency signals to one said electrode and to said resistance-capacitance network, said signals being 180° out-of-phase, a phase amplitude detector connected to said lines, and computer means connected to said detector for controlling the variation of resistance and capacitance in said network to obtain a zero volt reading at the input to said detector.

9. The probe system of claim 8 including means for applying from said oscillator a plurality of different frequencies of radio-frequency current to said electrodes, for enabling the accurate determination of soil capacitance at said different frequencies, and means in said second circuit portion for determining from the soil capacitance the dielectric dispersion characteristics of said soil.

10. The probe system of claim 8 wherein said phase amplitude detector is connected to said initial electronic portion through a high-pass filter.

11. The probe system of claim 8 wherein said computer controls the D-C bias power supplies.

12. A soil probe system, comprising a probe member having a tubular cylindrical shank portion made of insulating material and terminating at its lower end in a generally sharp circular edge, for penetrating soil along the cylindrical axis of said probe member, beginning with said edge, a pair of metal, electrically conductive, soil-contacting electrodes mounted in said cylindrical portion flush with the inner surface of said cylindrical portion, said electrodes being on the same horizontal level a short distance above said edge, and a third electrode mounted in said cylindrical portion vertically above one of said pair of electrodes, all of said electrodes being spaced apart from each other by said insulating material of said cylindrical portion, and an electrical-electronic measuring system having an initial portion in said shank above and connected to said electrodes by conducting means providing identical line impedances between each electrode and said system, a mirror image group of three auxiliary electrodes corresponding in size, shape, and location to the three soil-contacting electrodes above said initial portion and connected thereto by identical line impedances, said measuring system including means for balancing in air said soil-contacting electrodes with said mirror image group, said initial electronic portion being close to all said electrodes so as to minimize line impedance, said initial portion including a resistance-capacitance network connected to all of said electrodes and supplied with one D-C bias power supply for said resistance and another D-C bias power supply for said capacitance, said network having means for varying said resistance and capacitance, said measuring system also having a second portion distant from said cylindrical portion and connected to said initial electronic portion by lines having identical line impedance, for receiving said electronic signals and manipulating them electronically to produce data output, said second portion including an oscillator supplying radio-frequency signals to one said electrode and to a resistance-capacitance network, said signals being 180° out-of-phase, a phase amplitude detector connected to said lines, and computer means connected to said detector for controlling the variation of resistance and capacitance in said network to obtain a zero volt reading at the input to said detector.

13. The probe system of claim 12 including means for applying from said oscillator a plurality of different frequencies of radio-frequency current to said electrodes, for enabling the accurate determination of soil capacitance at said different frequencies, and means in said second circuit portion for determining from the soil capacitance the dielectric dispersion characteristics of said soil.

14. The probe system of claim 12 wherein said phase amplitude detector is connected to said initial electronic portion through a high-pass filter.

15. The probe system of claim 12 wherein said computer controls the D-C bias power supplies.

16. A soil probe system comprising a hollow, tubular cylindrical member made of insulating material, for penetrating soil in a direction along the axis of said cylindrical member, said member having a lower end which first enters the soil during penetration, three soil-contacting electrically conductive electrodes adjacent to the lower end of said cylindrical member, two on the same horizontal level and one spaced thereabove, said electrodes being mounted in said cylindrical member a short distance above its lower end, an electrical-electronic measuring system for measuring soil capacitance, connected to said electrodes by conducting means said measuring system having an initial electronic portion inside said cylindrical member and close to said electrodes said initial portion supplying electrical voltages at radio frequencies to said electrodes and receiving electrical signals from said electrodes and having means for generating related electronic signals, a second portion of said measuring system distant from said cylindrical member and connected thereto for sending signals at a wide range of radio frequencies to said initial portion, whence they go to said electrodes, and for receiving said electronic signals from said initial portion and manipulating them electronically to produce data output, three other electrodes mounted in said cylindrical member above said initial electronic portion in mirror-image relation to said soil-contacting electrodes and connected to said initial portion by lines having identical line impedance to the lines connecting said initial portion to said soil-contacting electrodes, and means for balancing in air said three soil-contacting electrodes with said three other electrodes.

17. A soil probe system comprising a hollow, tubular cylindrical member made of insulating material, for penetrating soil in a direction along the axis of said cylindrical member, said member having a lower end that first enters the soil during penetration, at least two electrically conductive electrodes mounted in said cylindrical member a short distance above its lower end, and an electrical-electronic measuring system connected to said electrodes and comprising, an initial electronic portion of said measuring system inside said tubular cylindrical portion and close to said electrodes, said initial portion including a resistance-capacitance network supplied with one D-C bias voltage for said resistance and another D-C bias voltage for said capacitance, said network having means for varying the resistance and the capacitance, said measuring system also having a second portion distant from said cylindrical portion and connected to said initial electronic portion by lines having identical line impedance, for supplying radio frequency signals 180° out-of-phase with each other to said network, for receiving said electronic signals, and for manipulating them electronically to produce data output, said second portion including an oscillator supplying radio-frequency signals to said electrodes and to said network, a phase amplitude detector connected to said lines, and computer means connected to said detector for controlling the variation of resistance and capacitance in said network to obtain balance in said bias voltages to preserve the 180° phase difference.

18. A soil probe system comprising a hollow, tubular cylindrical member terminating at its lower end in a conical portion, said member being made of insulating material, and used for penetrating soil along the axis of said member with said conical portion penetrating first, a pair of metal, electrically conductive, ring electrodes mounted in said cylindrical member a short distance above said conical portion, said ring electrodes lying flush with the outer surface of said cylindrical member and contacting said soil during said penetration and spaced apart from each other by said insulating material, and an electrical-electronic measuring system connected to said electrodes and comprising, an initial electronic portion of said measuring system inside said tubular cylindrical portion and close to said electrodes, said initial portion including a resistance-capacitance network supplied with one D-C bias voltage for said resistance and another D-C bias voltage for said capacitance, said network having means for varying said resistance and capacitance therein, said measuring system also having a second portion distant from said cylindrical portion and connected to said initial electronic portion for receiving said electronic signals and manipulating them electrically to produce data output, said second portion including an oscillator supplying radio-frequency signals to said electrodes, said signals being 180° out-of-phase, a phase amplitude detector connected to said lines, and computer means connected to said detector for controlling the variation of resistance and capacitance in said network to obtain balance in said bias voltages to preserve the 180° phase difference.

19. A soil probe system, comprising a probe member for said penetration having a tubular cylindrical portion made of insulating material and terminating at its lower end in a metal conical portion which first penetrates the soil, said member penetrating the soil along the cylindrical axis of said member, a pair of soil-contacting metal, electrically conductive, ring electrodes mounted in said cylindrical portion a short distance above said conical portion, the outer surfaces of said ring electrodes lying flush with the outer surface of the cylindrical portion and spaced apart from each other by said insulating material of said cylindrical portion, and an electrical-electronic measuring system connected to said electrodes and having an initial electronic portion inside said tubular cylindrical portion and close to said electrodes, said initial portion including a resistance-capacitance network connected to one said electrode and supplied with one D-C bias power supply for said resistance and another D-C bias power supply for said capacitance, said network having means for varying the resistance and the capacitance therein, said measuring system also having a second portion distant from said cylindrical portion and connected to said initial electronic portion for receiving said electronic signals and manipulating them electronically to produce data output, said second portion including an oscillator supplying radio-frequency signals to one said electrode and to said resistance-capacitance network, said signals being 180° out-of-phase, a phase amplitude detector connected to said lines, and computer means connected to said detector for controlling the variation of resistance and capacitance in said network to obtain a zero volt reading at the input to said detector.

20. A soil probe system, comprising a probe member having a tubular cylindrical shank portion made of insulating material and terminating at its lower end in a generally sharp circular edge, for penetrating soil along the cylindrical axis of said probe member, beginning with said edge, a pair of metal, electrically conductive, soil-contacting electrodes mounted in said cylindrical portion flush with the inner surface of said cylindrical portion, said electrodes being on the same horizontal level a short distance above said edge, and a third electrode mounted in said cylindrical portion vertically above one of said pair of electrodes, all of said electrodes being spaced apart from each other by said insulating material of said cylindrical portion, and an electrical-electronic measuring system having an initial portion in said shank above and connected to said electrodes, a mirror image group of three auxiliary electrodes corresponding in size, shape, and location to the three soil-contacting electrodes above said initial portion and connected thereto by identical line impedances, said measuring system including means for balancing in air said soil-contacting electrodes with said mirror image group, said initial electronic portion being close to all said electrodes, said initial portion including a resistance-capacitance network connected to all of said electrodes and supplied with one D-C bias power supply for said resistance and another D-C bias power supply for said capacitance, said network having means for varying said resistance and capacitance, said measuring system also having a second portion distant from said cylindrical portion and connected to said initial electronic portion impedance, for receiving said electronic signals and them electronically to produce data output, said second portion including an oscillator supplying radio-frequency signals to one said electrode and to a resistance-capacitance network, said signals being 180° out-of-phase, a phase amplitude detector connected to said lines, and computer means connected to said detector for controlling the variation of resistance and capacitance in said network to obtain a zero volt reading at the input to said detector.

* * * * *